United States Patent
Stubbers et al.

(10) Patent No.: US 8,309,342 B2
(45) Date of Patent: Nov. 13, 2012

(54) APPARATUS AND METHODS FOR CELL ISOLATION

(75) Inventors: Ron Stubbers, Houston, TX (US); Michael E. Coleman, Houston, TX (US)

(73) Assignee: InGeneron, Inc., Houston, TX (US)

( * ) Notice: Subject to any disclaimer, the term of this patent is extended or adjusted under 35 U.S.C. 154(b) by 0 days.

(21) Appl. No.: 12/746,334

(22) PCT Filed: Dec. 3, 2008

(86) PCT No.: PCT/US2008/085407
§ 371 (c)(1),
(2), (4) Date: Jun. 4, 2010

(87) PCT Pub. No.: WO2009/073724
PCT Pub. Date: Jun. 11, 2009

(65) Prior Publication Data
US 2010/0285588 A1    Nov. 11, 2010

Related U.S. Application Data

(60) Provisional application No. 61/005,267, filed on Dec. 4, 2007, provisional application No. 61/091,687, filed on Aug. 25, 2008.

(51) Int. Cl.
*C12P 1/00* (2006.01)
*C12M 1/00* (2006.01)
(52) U.S. Cl. ..................................... 435/267; 435/283.1
(58) Field of Classification Search .................. None
See application file for complete search history.

(56) References Cited

U.S. PATENT DOCUMENTS

| | | | | |
|---|---|---|---|---|
| 5,035,708 A | * | 7/1991 | Alchas et al. ................. | 623/1.45 |
| 5,079,160 A | * | 1/1992 | Lacy et al. ..................... | 435/381 |
| 5,372,945 A | * | 12/1994 | Alchas et al. ................. | 435/267 |
| 5,409,833 A | | 4/1995 | Hu et al. | |
| 5,486,359 A | | 1/1996 | Caplan et al. | |
| 5,756,291 A | | 5/1998 | Griffin et al. | |
| 5,786,207 A | * | 7/1998 | Katz et al. ..................... | 435/267 |
| 5,800,537 A | | 9/1998 | Bell | |
| 5,837,539 A | | 11/1998 | Caplan et al. | |
| 5,877,299 A | | 3/1999 | Thomas et al. | |

(Continued)

FOREIGN PATENT DOCUMENTS
WO  WO 2007/009036  1/2007

OTHER PUBLICATIONS

Dominici et al., "Minimal criteria for defining multipotent mesenchymal stromal cells. The International Society for Cellular Therapy position statement," *Cytotherapy*, 2006, 8:315-317.

(Continued)

*Primary Examiner* — James Ketter
*Assistant Examiner* — Reza Ghafoorian
(74) *Attorney, Agent, or Firm* — Fish & Richardson P.C.

(57) ABSTRACT

A unitary apparatus for isolating cells from adipose tissue including a lipid separation processor with a dispersing head equipped with a plurality of ports and a digestion chamber for dissociation of the constituent cells disposed in adipose tissue. The lipid separating apparatus is useful for the separation of lipids and adipocytes from a mixed cell population. A cell seeding chamber may be attached to the cell isolation apparatus. The components of the apparatus may be packaged in modular kit form.

14 Claims, 14 Drawing Sheets

U.S. PATENT DOCUMENTS

| | | | |
|---|---|---|---|
| 6,117,985 | A | 9/2000 | Thomas et al. |
| 6,139,757 | A * | 10/2000 | Ohmura et al. ............... 210/797 |
| 6,153,432 | A | 11/2000 | Halvorsen et al. |
| 6,306,575 | B1 | 10/2001 | Thomas et al. |
| 6,316,247 | B1 * | 11/2001 | Katz et al. ..................... 435/267 |
| 6,342,344 | B1 | 1/2002 | Thomas et al. |
| 6,391,297 | B1 | 5/2002 | Halvorsen |
| 6,429,013 | B1 | 8/2002 | Halvorsen et al. |
| 6,482,926 | B1 | 11/2002 | Thomas et al. |
| 6,491,918 | B1 | 12/2002 | Thomas et al. |
| 6,805,860 | B1 | 10/2004 | Alt |
| 6,867,289 | B1 | 3/2005 | Gorenstein et al. |
| 7,160,553 | B2 | 1/2007 | Gibbons et al. |
| 7,358,284 | B2 | 4/2008 | Griffey et al. |
| 7,390,484 | B2 | 6/2008 | Fraser et al. |
| 7,452,532 | B2 | 11/2008 | Alt |
| 2002/0033367 | A1 * | 3/2002 | Prince et al. .................. 210/650 |
| 2005/0084961 | A1 * | 4/2005 | Hedrick et al. ............... 435/366 |
| 2005/0153442 | A1 | 7/2005 | Katz et al. |
| 2006/0141623 | A1 | 6/2006 | Smith et al. |
| 2010/0124563 | A1 | 5/2010 | Coleman et al. |

OTHER PUBLICATIONS

International Bureau of WIPO, International Preliminary Report on Patentability and Written Opinion, mailed Jun. 17, 2010, 11 pages.

International Bureau of WIPO, International Search Report and Written Opinion, Jan. 19, 2009, mailed Feb. 23, 2009, 12 pages.

European Patent Office, Supplementary European Search Report, EP Application No. 08856235.0, mailed Oct. 14, 2011, 6 pages.

Altman et al. "Dermal matrix as a carrier for in vivo delivery of human adipose-derived stem cells," *Biomaterials*, 2008, 29(10):1431-1442.

Bai et al. "Electrophysiological Properties of Human Adipose Tissue-Derived Stem Cells," *Am J Physiol Cell Physiol*, 2007, 293(5):CI539-50.

Boquest et al "Isolation and transcription profiling of purified uncultured human stromal stem cells: Alteration of gene expression after in vitro cell culture," *Mol. Biol Cell*, 2005 16(3):1131-1141.

Cowan et al., "Adipose-derived adult stromal cells heal critical-size mouse calvarial defects," *Nat Biotechnol*, 2004, 22(5):560e7.

Erdag and Sheridan, "Fibroblasts improve performance of cultured composite skin substitutes on athymic mice," *Burns*, 2004, 30(4): 322e8.

Fuchs et al., "Diaphragmatic reconstruction with autologous tendon engineered from mesenchymal amniocytes," *J Pediatr Surg*, 2004, 39(6): 834-8.

Gimble and Guilak, "Adipose-derived adult stem cells: isolation, characterization, and differentiation potential," *Cytotherapy*, 2003, 5(5):362-369.

Gobin et al., "Repair and regeneration of the abdominal wall musculofascial defect using silk fibroin-chitosan blend," *Tissue Eng*, 2006, 12(12): 3383-3394.

Griffiths et al., "Survival of Apligraf in acute human wounds" *Tissue Eng*, 2004, 10(7-8):1180.

Hauner et al., "Promoting effect of glucocorticoids on the differentiation of human adipocyte precursor cells cultured in a chemically defined medium," *J. Clin. Invest.*, Nov. 1989, 84(5):1663-70.

Hewett et al., "Isolation and characterization of microvessel endothelial cells from human mammary adipose tissue," *In Vitro Cell. Dev. Biol.*, 1992, 29:325-331.

Hollenberg and Yost, "Regulation of DNA synthesis in fat cells and stromal elements from rat adipose tissue," J. Clin. Invest., 1968, 47: 2485-2498.

Kern et al., "Isolation and culture of microvascular endothelium from adipose tissue," *J. Clin. Invest.*, 1983, 71: 1822-1829.

Khor and Lim, "Implantable applications of chitin and chitosan." *Biomaterials*, 2003, 24(13):2339-2349.

Kim et al., "Wound healing effect of adipose-derived stem cells: A critical role of secretory factors on human dermal fibroblasts." *J Dermatol Sci*, 2007, 48(1):15-24.

Kim et al. "Direct comparison of human mesenchymal stem cells derived from adipose tissues and bone marrow III mediating neovascularization in response to vascular ischemia," *Cell Physiol Biochem*, 2007, 20(6): 867-876.

Prockop, "Stemness" does not explain the repair of many tissues by mesenchymal stem/multipotent stromal cells (MSCs), *Clin Pharmacol Ther.*, Sep. 2007, 82(3):241-3.

Rodbell, "Metabolism of isolated fat cells: Effects of hormones on glucose metabolism and lipolysis," *J. Biol. Chem*, 1964, 239: 375-380.

Van et al., "Cytological and enzymological characterization of adult human adipocyte precursors in culture," *J. Clin. Invest.*, 1976, 58: 699-704.

Wagner and Matthews, "The isolation and culture of capillary endothelium from epidymal fat," *Microvasc. Res.*, 1975, 10: 286-297.

Wu, et al. "Mesenchymal stem cells enhance wound healing through differentiation and angiogenesis" *Stem Cells*, 2007, 25(10): 2648-59.

Zhang et al. "Transduction of bone-marrow derived mesenchymal stem cells by using lentivirus vectors pseudotypes with modified RD114 envelope glycoprotains," *J. Viral.*, 2004, 78: 1219-29.

Zuk et al "Human Adipose Tissue is a Source of Multipotent Stem Cells," *Mol. Biol. Cell*, 2002, 13: 4279-95.

* cited by examiner

Figure 15A

| Sample | anti-CD31 | anti-CD34 | anti-CD44 | anti-CD45 | anti-CD71 | anti-CD73 | anti-CD90 | anti-CD105 | anti-CD117 | anti-CD146 | anti-Sca-1 | anti-SSEA-4 |
|---|---|---|---|---|---|---|---|---|---|---|---|---|
| Adherent | 5.36 | 85.3 | 88.6 | 6.07 | 44.1 | 77.9 | 76.5 | 4.17 | 2.21 | 7.74 | 8.84 | 3.84 |
| Non-adherent | 15.7 | 72.8 | 62.3 | 36.4 | 40 | 12.3 | 23.4 | 2.3 | 0 | 3.9 | 1.4 | 3.7 |

Total Yield – 40.2 x 10⁶/100 g
Viability – 93 %
Percent Adherent – 81 %

Figure 15B

| Sample | anti-CD31 | anti-CD34 | anti-CD44 | anti-CD45 | anti-CD71 | anti-CD73 | anti-CD90 | anti-CD105 | anti-CD117 | anti-CD146 | anti-Sca-1 | anti-SSEA-4 |
|---|---|---|---|---|---|---|---|---|---|---|---|---|
| Adherent | 2.86 | 90.1 | 92.4 | 2.88 | 2.93 | 50.6 | 91.2 | 4.91 | 0.2 | 3.31 | 0.68 | 0.53 |
| Non-adherent | 34.65 | 61.2 | 38.8 | 41.9 | 17.8 | 13 | 50.7 | 1.95 | 0.78 | 16.55 | 0.19 | 21.65 |

Total Yield – 9.7 x 10⁶/100 g
Viability – 87 %
Percent Adherent – 76 %

Figure 15C

| Sample | anti-CD31 | anti-CD34 | anti-CD44 | anti-CD45 | anti-CD71 | anti-CD73 | anti-CD90 | anti-CD105 | anti-CD117 | anti-CD146 | anti-Sca-1 | anti-SSEA-4 |
|---|---|---|---|---|---|---|---|---|---|---|---|---|
| Fresh | 40.1 | 45.9 | 46.3 | 20.3 | 16.5 | 32.6 | 41.3 | 0 | 0 | 26.1 | 0 | 8.3 |

Total Yield 118.4 x 10⁶/100 g

APPARATUS AND METHODS FOR CELL ISOLATION

CROSS REFERENCE TO RELATED APPLICATIONS

This application is a National Stage application under 35 U.S.C. §371 and claims the benefit of International Application No. PCT/US2008/085407, having an International Filing Date of Dec. 3, 2008, which claims priority based on United States Provisional Application No. 61/005,267, filed Dec. 4, 2007, and U.S. Provisional Application No. 61/091,687, filed Aug. 25, 2008, the entireties of which are incorporated herein by reference.

FIELD OF THE INVENTION

This invention relates generally to apparatus and methods for cell isolation. The present invention relates more particularly to apparatus and methods for efficient isolation of useful cell populations from lipoaspirate.

BACKGROUND OF THE INVENTION

Without limiting the scope of the invention, its background is described in connection with existing isolation and uses of reparative cell populations including preadipocytes, fibroblasts, pluripotent stem cells, endothelial cells, endothelial progenitor cells, and other supporting cell types. Isolated, or purified cell populations, have been shown to have various potential therapeutic applications. Preadipocytes may provide a durable filler for wrinkles or other cosmetic skin defects, fibroblasts may have utility to treat wrinkles and skin wounds, endothelial cells and endothelial progenitor cells may contribute to neovascularization supplying oxygenated blood to ischemic tissue, and pluripotent stem cells, due to their ability to differentiate into various cell types and tissues, may have the capacity to treat a number of conditions.

Mesenchymal stromal cells (MSC), originally isolated from bone marrow, are considered to be pluripotent and are thus potentially able to differentiate into a myriad of cell types including osteoblasts, chondrocytes, myocytes, adipocytes, and islet cells. More recently it has been found that MSC can also be isolated from the stroma of adipose tissue, which is considerably more readily obtained than is bone marrow. Indeed, by virtue of its relatively high content of MSCs, adipose tissue has been shown to be a convenient source of cells that have shown utility for cell therapy, at least in a research setting. Like MSC from bone marrow, adipose derived MSC, or "ADSC" are pluripotent. ADSC have recently yielded cell preparations useful for the repair of articular cartilage. Additionally, these stromal cells have been cultured to differentiate into cells having neuronal characteristics. Finally, ADSC have been used as a source in generating hematopoietic cells, osteogenic cells, endothelial cells, adipocytes and myocytes of skeletal and smooth muscle.

In addition to ADSC, adipose tissue is also a rich source of other cell types that may have utility in treatment of various medical conditions. Adipose tissue is a rich source of preadipocytes, fibroblasts, endothelial cells, and endothelial progenitor cells. While existing methods have allowed considerable study of isolated therapeutic cells in research environments, methods and apparatus for isolation in sufficient quantity and quality for clinical use have been problematic and continue to represent an unmet need. For example, current methods used in cell isolation and purification frequently use cell culturing. The required use of cell culturing is fairly impractical in a clinical setting wherein one might desire a rapid source of fresh cells that have a clinically useful composition. Cell sorting techniques using flow cytometry in conjunction with fluorescence tagging or magnetic affinity are also currently used and enable the isolation of cell subpopulations of good homogeneity, but these approaches are slow and impractical for obtaining large, useful cell preparations for tissue repair in a reasonable time scale. Many separation technologies also require centrifugation equipment further adding to the complexity of the process as well as increasing capital investment cost.

Devices for isolation of particular cell populations from adipose tissue have been previously described. Alchas et. al. described a device and method for collecting and processing fat tissue and procuring microvessel endothelial cells in U.S. Pat. No. 5,372,945 and an endothelial cell procurement and deposition kit in U.S. Pat. No. 5,035,708. Hu et. al. described a microvessel cell isolation apparatus in U.S. Pat. No. 5,409,833. The devices described by Alchas et al. and Hu et al. were designed to specifically isolate microvessel endothelial cells. Katz et al described adipose tissue dissociating systems and methods in U.S. Pat. Nos. 5,786,207 and 6,316,247. Fraser et al. disclosed systems and methods for separating and concentrating regenerative cells from adipose tissue in U.S. Pat. No. 7,390,484. These devices all incorporate centrifugation in the process of separating non-adipocyte cells from lipid filled adipocytes.

The use of cell preparations for therapeutic application, such as tissue repair, may be complicated by the presence of other cell types depending on the medical application. For example, the presence of leukocytes may cause immune system inflammatory problems in certain indications. This could be life threatening when the cell preparation is used in tissue repair in the heart, for example. Likewise, it may be desirable to remove erythrocytes to avoid problems related to incompatible blood group types or their involvement in thrombus formation.

In light of the foregoing, it would be beneficial to develop a system for isolating and purifying cell populations in good yields in clinical settings, which require isolation in a relatively rapid time frame. Such a system would benefit from flexibility in components to address the need for different cell subpopulations according to medical application which may span from life threatening ischemic events to cosmetic surgery. The introduction and acceptance of such new technologies into clinical practice is dependent on their cost effectiveness, safety, and ease of use.

The present invention provides several important advantages over existing technology. First, the present invention provide for a simple method to efficiently separate the non-adipocyte cell fraction from the significant fraction of lipid-filled adipocytes and oil present in a cell mixture that results from disaggregated adipose tissue or lipoaspirate. This improvement reduces complexity and capital equipment requirements. Second, the present invention offers the end user a simplified form factor such as a uniform cylinder that can be easily integrated with typical lipoaspiration equipment in clinical use. The present invention has been shown to be particularly effective in rapid and efficient isolation of desirable cell populations for use as autografts in target tissues.

BRIEF SUMMARY OF THE INVENTION

In one aspect, the present disclosure provides an apparatus for isolating cells from adipose tissue that includes a lipid separating apparatus having one or more dispersing ports equipped with a plurality of pores (or other means of dispersion) and a cell separation assembly that includes a plurality of optionally removable filters of variable pore size. The cell separation assembly may be arranged to interface with a lipoaspiration device and to selectively separate and elute cells.

In a particular aspect, the present disclosure provides an apparatus for isolating cells from adipose tissue that includes a container having a plurality of ports, a first filter that may be removably connected to one of the plurality of ports at one end and may be removably connected to a fat separating apparatus at the opposing end of the first filter.

The fat separating apparatus includes one or more dispersing ports having a plurality of pores, an optionally removable second filter and an outlet end disposed below, proximal to the dispersing ports. The fat separating apparatus is useful for the separation of lipids and adipocytes from a mixed cell population. It includes a container having a top and bottom and the dispersing port disposed proximal to the bottom of the container, and optionally a filter disposed proximal to the bottom of the container but not in the flow path of the dispersing port. The fat separating apparatus may be used independently in other applications that require lipid separations from aqueous media.

In some aspects, embodiments of the apparatus may include a series of concentric chambers that is designed to interface with a lipoaspiration unit, thus allowing a person to collect samples for on-demand separation of cell populations for immediate use. In other embodiments, such an apparatus may also be equipped with a means for longer-term storage of collected lipoaspirate.

In one embodiment of the invention, a modular kit is provided that may be constructed by including components of a modular apparatus in the kit. Any and all of the components may be disposable.

In one embodiment of the invention, a method is provided of preparing a population of cells for cell transplantation into a patient in need thereof including dissociating a sample of donor adipose tissue into individual cells and small clusters of cells until the dissociated cells and clusters of cells are reduced in diameter to about 1000 microns or less, phase separating the individual cells and small clusters of cells into an aqueous cellular layer and a lipid layer without centrifugation, and collecting cells for cell transplantation from the aqueous cellular layer. In further embodiments, the dissociated cells and clusters of cells are reduced in diameter to about 500 microns or less or are reduced in diameter to about 250 microns or less. In one embodiment the collected cells for cell transplantation include stromal vascular fraction cells.

Also provided is an apparatus for recovering stromal vascular cells from adipose tissue, wherein the apparatus includes a container adapted for processing adipose tissue into individual cells and small clusters of cells to a diameter of about 1000 microns or less and a lipid separating unit adapted to separate the processed adipose tissue without the need for centrifugation into a lipid layer enriched in adipocytes and an aqueous layer enriched in stromal vascular fraction cells.

In one embodiment of the invention a method is provided for separating adipocytes from a population of cells that includes adipocytes. In accordance with the method, a population of cells that includes adipocytes is introduced into a lipid separating unit in an aqueous medium. The lipid and lipid containing cells float upward forming a top lipid layer in the lipid separating unit while the non-lipid containing or non-adipocyte cells float downward under the influence of gravity and can be withdrawn from under the top lipid layer. In accordance with this method, non-adipocytes can be separated from lipid containing cells without centrifugation. In a further embodiment, the population of cells that includes adipocytes is introduced into the lipid separating unit through a dispersing head that includes a plurality of pores that are dimensioned to separate cell clumps. In certain embodiments, the population of cells that includes adipocytes is filtered to reduce cell clumps prior to introduction into the lipid separating unit such that potential clogging of the dispersing head can be avoided.

In one embodiment of the invention a method is provided for separating cells from a tissue including the steps of introducing a tissue into a digestion chamber that includes a digestion fluid and an internal digestion mesh, recirculating the digestion fluid across the digestion mesh until the tissue is separated into a digestion mixture that includes individual cells and cell clusters, followed by phase separating the digestion mixture through an aqueous medium disposed in a lipid separating unit. After the phase separation, wherein the constituent cells of the digestion mixture are separated on the basis of density in an aqueous medium, desired cell populations can be collected from below the floating lipids and lipid containing cells within the separating unit. Isolation of desired cell populations is accomplished in a unitary device without a need for centrifugation. In further embodiments, the digestion mixture is filtered over at least one dispersing filter prior to phase separating. In certain embodiments the digestion mixture is conveyed through a dispersing head disposed within the separating unit, said dispersing head forming an entry port that is able to further divide clumps of cells within the digestion mixture as the digestion mixture enters the separation unit. In certain embodiments, the digestion chamber is agitated during tissue separation, the agitation being useful to further disrupt clusters of cells and to prevent clogging of the digestion mesh. The method is particularly suitable isolation of cells from adipose-containing tissues of human, equine, canine, feline, porcine, murine, simian, caprine, and ovine origin.

In certain embodiments of the invention, a unitary disposable apparatus is provided for recovering cells from a biological tissue without a need for centrifugation. In one embodiment, the apparatus includes a digestion chamber adapted to receive and dissociate the biological tissue into a digestion mixture including cells and cell clusters and a lipid separating unit in fluid communication with the digestion chamber and adapted for phase separation of the digestion mixture into an aqueous cellular layer and a lipid layer that includes free lipids and cells that contain lipid droplets such as adipocytes. By aqueous cellular layer it is meant a layer of cells that lack internal lipid droplets as are found in adipocytes. In one embodiment, the digestion chamber of the apparatus is divided by an internal digestion mesh into post-digestion chamber and a predigestion chamber. The digestion chamber and associated fluid conduits are adapted to provide a recirculating fluid path through the pre-digestion and post-digestion chambers via a recirculating tubing circuit. Typically, a motive force for a fluid flow through the apparatus is provided by one or more pumps.

In certain embodiments a heat exchanger is disposed in functional communication with the recirculating tubing circuit and the fluid flow is directed through the heat exchanger by the motive force of the one or more pumps. The heat exchanger is able to adapt the temperature of fluid flowing through the digestion chamber and thereby control activity of digestion enzymes utilized to digest the connective tissues that hold the tissue together. In certain embodiments, the one or more pumps and the heating exchanger are external to the apparatus and the apparatus is a one-time use disposable unit.

In one useful configuration, the internal digestion mesh is fixed in a vertical cylindrical orientation within the digestion chamber such that the pre-digestion chamber and the post-digestion chamber are in a concentric orientation. In one particular embodiment the outer concentric chamber is the predigestion chamber and the inner chamber is the post digestion chamber. In this configuration a maximum surface area and exposure to fluid flow is provided to the pre-digested tissue and clogging of the digestion mesh is minimized. In certain embodiments, at least one dispersing filter is disposed in the fluid communication between the digestion chamber and the lipid separating unit. In one particular embodiment, at least one dispersing filter is disposed in a fixed horizontal plane and is arranged in a perpendicular orientation to the digestion mesh. In one particular embodiment, the apparatus is a unitary combination of digestion chamber, dispersing filter and lipid separating unit in a single sterilizable and disposable unit that forms closed flow path from the initial introduction of tissue into the unit until isolated individual cells and small clusters of cells are removed from the unit. In one embodiment of such an apparatus, the bottom of the digestion chamber forms a top of the lipid separating unit and the dispersing filter is disposed circumferentially, and integrated near a top aspect, of the lipid separating unit such that the surface area of the dispersing filter can be maximized and the size of the lipid separating unit can be minimized.

In one particular embodiment an apparatus for isolating cells from adipose containing tissue is provided that includes a digestion chamber divided by an internal digestion mesh into a post-digestion chamber and a concentric pre-digestion chamber. In this embodiment, the digestion chamber as a whole includes at least one inlet port configured to introduce adipose containing tissue into the pre-digestion chamber and at least one outlet port configured to recover a digested cell mixture out of the post-digestion chamber and a fluid conduit connecting the pre-digestion chamber and the post-digestion chamber and adapted to provide a recirculating fluid flow from the post-digestion chamber and back to the pre-digestion chamber. The post digestion chamber is in fluid communication with a lipid separating unit and the lipid separating unit has at least one dispersing port equipped with a plurality of dispersing pores through which the digested cell mixture enters the lipid separating unit. The pores of the dispersing port effect further disruption of cell clusters as they enter the lipid separating unit such that desired non-lipid containing cells are generally dissociated from the adipocytes. In one particular embodiment the dispersing port is located proximal to the bottom of the lipid separating unit and the pores are directed downward such that the flow path of the cell mixture out of the dispersing head maximizes fluid shear applied to the cells.

The lipid separating unit is adapted for phase separation of lipids and lipid containing cells from a population of non-lipid containing cells and includes a collection port disposed in the lipid separating unit to collect the population of non-lipid containing cells from under the floating lipid layer. When disposed in a unitary sterilizable apparatus having closed flow path, collection of various cells from adipose containing tissue is provided without a need for centrifugation. In one particular embodiment, at least one filter is disposed in the fluid flow path between the digestion chamber and the lipid separating unit. In one embodiment, apparatus includes a digestion mesh having a pore size of about 1000 microns, at least one dispersing filter having a pore size of about 250 microns and dispersing head having pores with a pore size of about 500 microns.

The foregoing has outlined rather broadly the features of the present invention in order that the detailed description of the invention that follows may be better understood. Additional features and advantages of the invention will be described hereinafter, which form the subject of the claims of the invention.

BRIEF DESCRIPTION OF THE DRAWINGS

The foregoing and other features and aspects of the present invention will be best understood with reference to the following detailed description of a specific embodiment of the invention, when read in conjunction with the accompanying drawings, wherein:

FIGS. 15A and B represent characterization data for reparative cell populations isolated according to the process depicted in FIG. 5 and separated into adherent and non-adherent populations prior to characterization. FIG. 15C represents characterization data for freshly isolated cells without adherent separation.

In FIG. 17 a series of selective seeding chambers are utilized in serial fashion for positive or negative selection or a combination thereof.

DETAILED DESCRIPTION OF THE INVENTION

Figure 1:
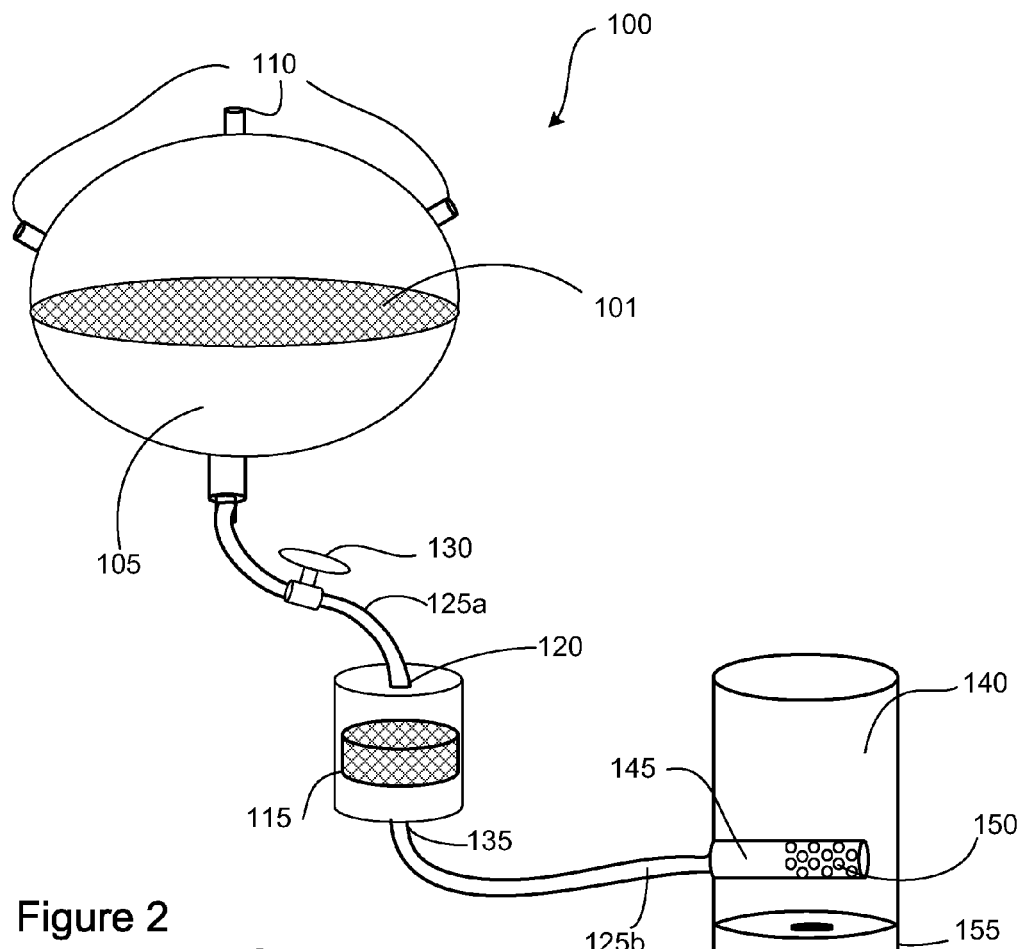
FIG. 1 is a diagram of a modular apparatus for cell preparation in accordance with embodiments of the present disclosure.

The present disclosure provides an apparatus which may be used in isolating sub-populations of cells from a mixture of cells, with the separation principles found herein below particularly suitable to be applied to the isolation of cells derived from adipose tissue. While the making and using of various embodiments of the present invention are discussed in detail below, it should be appreciated that the present invention provides many applicable inventive concepts, which can be employed in a wide variety of specific contexts. The specific embodiments discussed herein are merely illustrative of specific ways to make and use the invention and do not delimit the scope of the invention.

One can envision various applications for the apparatus and methods of the present invention. For instance, one can apply the apparatus and methods of the present invention to isolate stem cells from a human tissue in an expedited manner and utilize those stem cells soon after isolation for various therapies. By way of background, stem cells have the capacity for renewal through mitotic cell division and can differentiate into a diverse population of specialized cell types. In adult organisms, stem cells and progenitor cells act as a repair system for the body, replenishing specialized cells. Because stem cells can be readily grown and transformed through culturing into cells with characteristics of various tissues, such as muscles or nerves, their potential uses in therapeutic treatments are potentially numerous.

Stromal cells, for example, isolated from adipose tissue have recently yielded cell preparations useful for the repair of articular cartilage. Additionally, these stromal cells have been cultured to differentiate into cells having neuronal characteristics. Likewise, adipose-derived stromal cells have been used as a source in generating hematopoietic cells, osteogenic cells, endothelial cells, adipocytes and myocytes of skeletal and smooth muscle.

To facilitate the understanding of this invention, certain terms are defined. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term Mesenchymal Stromal Cell (MSC) means the definition adopted by the International Society for Cellular Therapy and published in a position paper by Dominici et al, Cytotherapy 8 (2006) 315. In accordance with the position paper, MSC must: 1) be plastic adherent when maintained in standard culture conditions, 2) must express CD73, CD90, and CD105, and must lack expression of the hematopoietic markers CD11b or CD14, CD34, CD45, CD79a or CD19 and HLA-DR surface molecules. MSC have been traditionally defined as spindle-shaped or fibroblast-like plastic adherent cells. Although originally isolated from bone marrow, MSC have now been isolated from a variety of tissues including bone periosteum, trabecular bone, adipose tissue, synovium, skeletal muscle, dental pulp and cord blood.

Adipose tissue is characterized by the presence of mature adipocytes bound in a connective tissue framework termed the "stroma." The stroma of adipose tissue includes an array of cells that do not include the lipid inclusions that characterize adipocytes. These include preadiopcytes, fibroblasts, vascular smooth muscle cells, endothelial cells, monocyte/macrophages and lymphocytes. When the connective tissue of adipose tissue is digested, such as with collagenase, the lipid containing adipocytes can be separated from the other cell types. The non-adipocyte fraction of cells isolated from adipose tissue by enzyme digestion has been termed the "stromal vascular fraction" or "SVF." Heretofore, adipocytes have been separated from the SVF by centrifugation wherein the adipocytes float and the cells of the SVF form a pellet. Typically however, the SVF is subject to further processing and selection, including plastic adherence. Cells from the stromal vascular fraction that have been subject to plastic adherence are typically referred to as cultured stromal vascular cells or "adipose tissue-derived stromal cells" (ADSC).

Not withstanding other definitions that may exist in the art, as used herein, the term "stromal vascular fraction cells" refers to all of the constituent cells of adipose tissue after enzyme digestion and removal of adipocytes and are not limited to plastic adherent cells.

As used herein, "reparative cell population" refers to a mixture of cells isolated from the SVF that includes "tissue engrafting cells" that are herein defined to include MSC as well as cells such as fibroblasts and endothelial cells that are able to proliferate and engraft a target tissue when returned to the body. The reparative cell population may also include one or more "supportive cell" populations. Supportive cells are herein defined as cells that do not engraft in the target tissue but may aid in the tissue remodeling process that is essential to healing of damaged tissue. These may include, for example, lymphocytes and macrophages. As used herein the term "reparative cell population" is not limited to plastic adherent cells and may be the same as stromal vascular fraction cells under some circumstances.

The methods and apparatus disclosed herein are designed for rapid preparation of cell sub-populations from a tissue source without the need for centrifugation. The apparatus may be modular in construction to incorporate different components, depending on factors such as degree of purity required and/or desired cell-type sub-population. Ideally, the components of the apparatus are all inexpensive and any of the individual components may be considered disposable.

Referring to the drawings wherein depicted elements are not necessarily shown to scale and wherein like or similar elements may be designated by the same reference numeral through several views.

Example 1

Isolation of Reparative Cells from Adipose Tissue

FIG. 1 is a perspective view of one embodiment of an apparatus 100 having a digestion chamber 105 equipped with one or more ports 110 into which an adipose tissue sample may be introduced. Several procedural steps in purification and isolation of cell subpopulations may be carried out in this container. One of the many ports 110 may deliver washed and dissociated materials to a first filter 115 which may be removably connected to the port at the filter's first end 120 via tubing 125a equipped with a valve 130 or the like. The second end 135 of first filter 115 may be removably connected via tubing 125b to a fat or lipid separating chamber or unit 140. The fat separating chamber has a dispersing head 145 having a plurality of dispersing pores 150 through which a lipid/adipocyte-containing aqueous emulsion is well-dispersed to aid phase separation. Proximal to the bottom of the fat separating chamber 140 is an outlet end 160, which may optionally include a second filter 155.

Outlet end 160 is capable of integration with further components as deemed necessary for a particular application such as on-site autologous cell therapy. In one embodiment, the apparatus may be further equipped with, for example, a diafiltration chamber (not shown) removably attached to the outlet end 160. Samples may be collected into an appropriate container which may be one that is suitable for banking of the purified and isolated cells or alternatively one that is suitable for clinical use.

Referring to the beginning of the separation process, digestion chamber 105 may be designed to carry out any number of operations including, but not limited to removal of excess fluid from a tissue sample, washing the tissue sample, performing enzymatic digestions, adding fluid or antibiotics, and positive and/or negative cell selection. Digestion chamber 105 may be flexible and bag-like, resembling an I.V. bag, for example. Alternatively, digestion chamber 105 may be rigid allowing for use of a vacuum source to facilitate, for example, removal of excess fluid from a sample, and optionally washing the tissue sample. Whether flexible or rigid, digestion chamber 105 may also include a filter mesh 101 to retain tissue but allow passage of fluid and dissociated cells.

Standard agents for performing tissue dissociation include commercially available preparations, such as Blendzyme formulations available from Roche Diagnostics (Indianapolis, Ind.), may be carried out in digestion chamber 105. The use of particular enzymes and protease compounds at particular concentrations in the separation process may be optimized to maximize the yield of specific cell subpopulations and provide them as a cellular suspension. Alternatively, one may use pure collagenase or a mixture of pure collagenase and other specific proteases, for example elastase, to carry out tissue dissociation. Digestion chamber 105 equipped with a filter mesh (as described above) may be used for manipulation of material, including the digestion fluid, by circulation. This may be accomplished by passing fluid in a port on one side of the mesh, through the material to be digested, and then extracting the material to be retained along with the digestion liquid from a port at the opposite side of the mesh.

Cell selection techniques may include, but are not limited to, the use of at least one immobilized biologic agent. The immobilized biologic agent may be an antibody (see U.S. Pat. Nos. 6,491,918, 6,482,926, 6,342,344, 6,306,575, 6,117,985, 5,877,299, and 5,837,539), an aptamer (see U.S. Pat. No. 5,756,291), and/or a thioaptamer (see U.S. Pat. No. 6,867, 289), for example, all of which are incorporated herein by reference in their entirety. The biologic agents may be immobilized on polymer beads, for example, and placed in container 105. The biologic agent may also be immobilized on the inner surface of container 105 to facilitate the cell selection. Alternatively, the agents could be placed on a matrix or on a scaffold. The various biologic agents may aid the depletion of leukocytes and/or erythrocytes, in one embodiment. It is also possible to use the biologic agents to specifically bind a desired cell type for isolation.

In one embodiment of the invention, after all of the desired digestion chamber 105 processes have been completed, the dissociated material may be optionally fed via tubing 125a to dispersing filter 115. Dispersing filter 115 generally has a pore size smaller than the size of the plurality of pores 150 of dispersing head 145 downstream in the apparatus. This arrangement avoids the potential problem of clogging the dispersing head pores. Additionally, dispersing filter 115 generally has a pore size greater than the pore size of an optional second filter 155 disposed near the bottom of fat separating chamber 140. In one embodiment, the pore sizes of dispersing filter 115 and second filter 155 are graduated in decreasing size to minimize material losses.

In one embodiment, dispersing filter 115 has a pore size ranging from about 100 microns to about 1 mm. In another embodiment, dispersing filter 115 has a pore size ranging from about 200 microns to about 300 microns. In yet another embodiment, the dispersing filter has an average pore size of about 265 microns.

Figure 2:
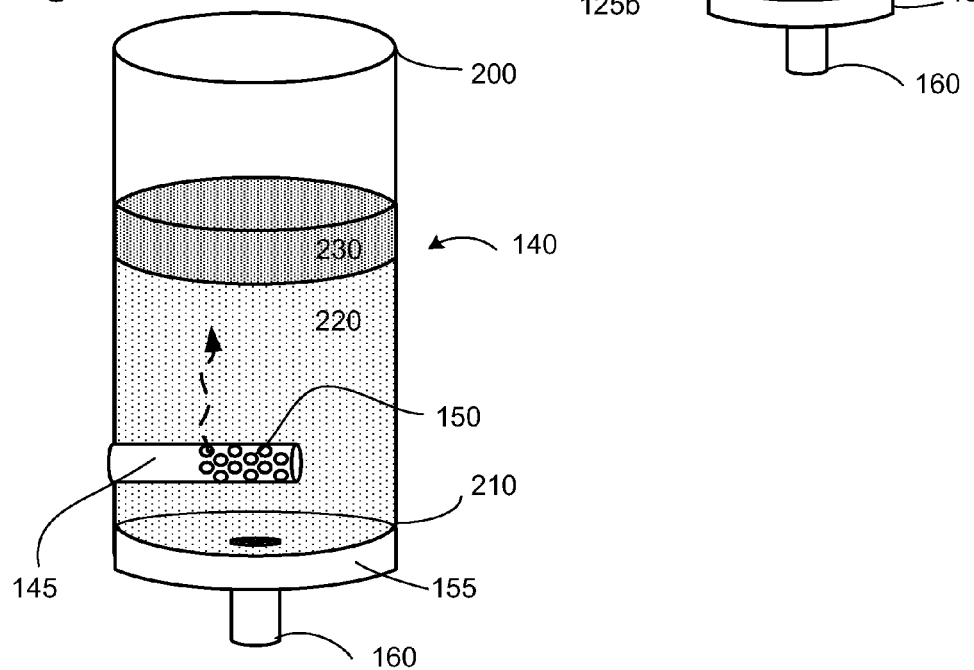
FIG. 2 is a close up of a lipid separation module, in accordance with one embodiment of the present disclosure.

After passing through dispersing filter 115, tubing 125b may be used to carry the resultant emulsion to fat separating unit 140, shown in expanded form in FIG. 2. Fat separating unit 140 is used to separate lipids and adipocytes from the mixed cell population. The unit is any type of a container having a top 200 and bottom 210. The container shape may be cylindrical, conical, or more generally narrowing from top 200 to bottom 210. Dispersing head 145 is generally located proximal to the bottom 210 and is equipped with a plurality of pores 150. The plurality of pores have a size ranging from about 300 microns to about 1000 microns, in one embodiment and from about 400 microns to about 600 microns in another embodiment. The average pore size of the dispersing ports is about 500 microns in a particular embodiment.

In operation, at least a portion of the fat separating unit 140 is filled with an aqueous media 220 through which the emulsion passes as it exits pores 150 of dispersing head 145. The dispersion of the emulsion facilitates separation of adipocytes/lipids as a separate layer 230 from the cells of interest by differential specific gravity. The lipids and adipocytes have a lower specific gravity and therefore, as depicted by the dashed line, float to the top generating layer 230, whereas the cells of interest and other small cells are either more dense or neutrally dense with respect to the media, and so remain in the media or settle to the bottom. This arrangement allows the media or other liquid containing the cells of interest to be collected via outlet 160, with most of the adipocytes and lipids remaining in layer 230. The apparatus could alternatively be equipped with a means to detect the interface between lipid phase 230 and aqueous phase 220. This detection means may rely on a colorimetric determination or by monitoring changes in density, for example. Fat separating chamber 140 may have near bottom 210 a second filter 155 in the system. The second filter has a pore size ranging from about 10 microns to about 100 microns in one embodiment and a pore size ranging from about 30 microns to about 50 microns in another embodiment. The average pore size is about 37 microns in a particular embodiment.

Other components may be present after outlet 160. These may include a diafiltration chamber, which may be removably attached from outlet end 160, and a variety of collection containers. The former may be useful in the concentration of the purified and isolated cell preparation. The latter may include containers that are appropriate for banking of the cells collected. The components of the apparatus as well as the post separation diafiltration chambers and collection containers may be packaged in kit form. Such a kit may, in conjunction with instructions, be operable by a trained technician for the rapid isolation of cell populations.

Figure 3:
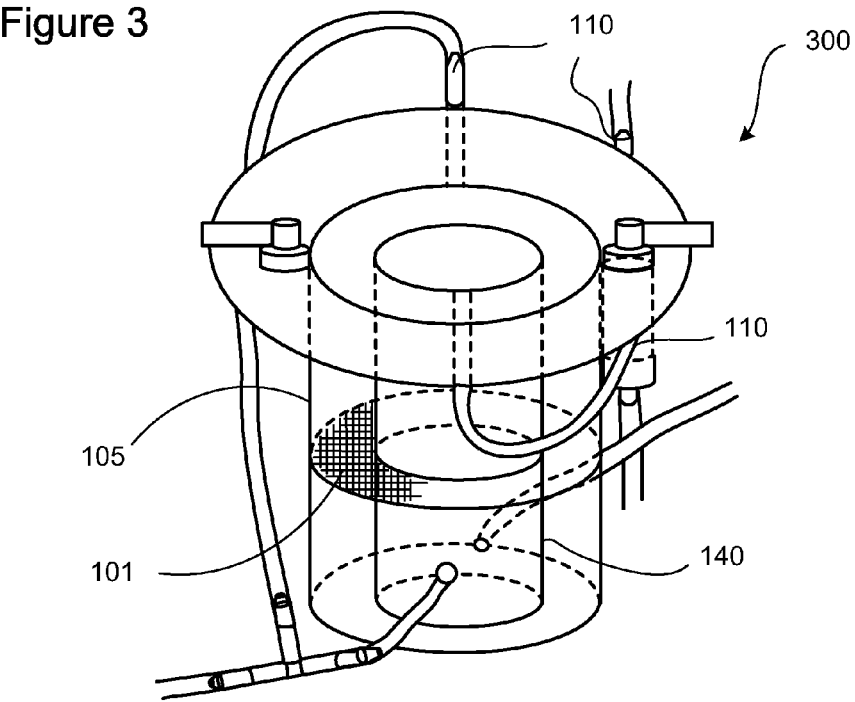
FIG. 3 is a view of an apparatus equipped for optional integration into a lipoaspiration unit.
Figure 4:
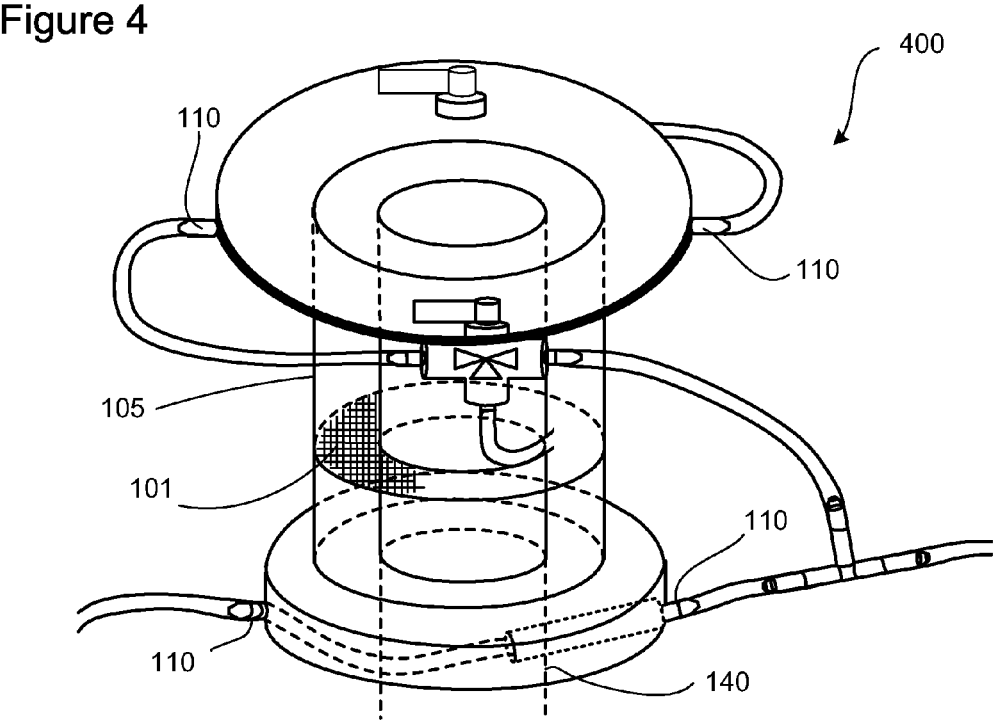
FIG. 4 is another view of the apparatus of FIG. 3.

In yet another embodiment, FIG. 3 shows an apparatus 300 (alternative view 400 in FIG. 4) that provides for isolating cells from adipose tissue with a different configuration of components. The apparatus 300 has a container with a plurality of ports. The apparatus may be designed for integration with a lipoaspiration unit. FIGS. 3 and 4 show configurations that would be compatible with such usage. Additionally, the apparatus may contain design features such as a bypass unit that allows for continued lipoaspiration when desired, for example after a determined amount of lipoaspirate has been collected into said apparatus 300. FIGS. 3 and 4 are configured in an arrangement having a plurality of concentric chambers. The apparatus 300 allows the unit to engage with a lipoaspirate collection unit. In a preferred embodiment, the apparatus 300 is self-contained with all the desired filters and the lipid separating assembly described hereinabove.

As depicted in the embodiment of FIG. 3, a plurality of connectors are included and are designed for passing a sample through each of the plurality of concentric chambers. The sample may be passed from the innermost chamber to the outermost chamber or vice versa.

In one embodiment, the chamber receiving the sample may be equipped with an initial filter for the first set of operations that may include selective removal of certain cell populations. Again this may be accomplished by the use of antibodies, aptamers, thioaptamers or the like. Depending on the workflow direction of the sample, each cylinder may be equipped with a means to keep the contents separated until such a time as the contents are ready to be passed through to the next concentric chamber. Such means includes, for example, stopcock valves, pinch valves, or ball valves.

It is desirable that the apparatus having concentric chambers be operable by a technician that can couple the assembly with a lipoaspiration unit, collect the sample, and perform the separation without material transfer to other containers. The assembly may be equipped with appropriate means for longer-term storage and transport of the assembly to another location, for example by securing the initially collected sample in the first chamber serving as the collection chamber. Each of the concentric chambers may be optionally connected via the top lid or bottom to further valves or ports for introducing material into or removing material from each of the concentric chambers.

Results:

One function of the devices presented hereinabove is to collect lipoaspirate and isolate within a closed system the stromal vascular fraction of cells. In the following experiment, the concentric cylindrical apparatus was used. Results depict the number of cells obtained from the stromal vascular fraction obtained from 100 grams lipoaspirate. Total nucleated cells within the stromal vascular fraction obtained from processing 100 grams lipoaspirate typically range from $5 \times 10^6$ to $50 \times 10^6$ cells. When plated onto tissue culture plates typically $2 \times 10^6$ to $20 \times 10^6$ adherent cells are obtained 12-18 h after plating. Cell number was determined using a hemacytometer with the results shown in Table 1.

TABLE 1

Pellet Weight & Cell Yield for 100 g of Fat

| Total Nucleated Cell Yield ($\times 10^6$) on Day 0 | Adherent Cell Yield ($\times 10^6$) on Day 1 |
| --- | --- |
| 9.2 | 7.4 |
| 24.7 | 13.4 |
| 6.2 | 6.8 |
| 2.2 | 2.7 |
| 12.9 | 7.8 |
| 4.9 | 2.0 |

Several aspects aided the separation process with an initial prototype device as follows: 1) Injection of the emulsion into the fat separating portion (fat digestion chamber) of the device is preferably made into a volume of some type of media. Volume is less critical than height of the media. 2) For the separator system, to actually disaggregate the tissue, agitation, and preferably agitation and recirculation or forced movement of the digestion fluid may be used. 3) It was determined that for digestion to take place using the variations of the prototype digestion container that were tested, a mesh of about 1 mm pore size was effective to prevent clogging and allowed the cells and fluid to pass, but did not allow the lumps and undigested connective tissue to pass. Having the cylindrical drain in the middle of the apparatus provided better results.

In one embodiment, apparatus configurations described hereinabove may be used for isolating cells from living tissue to yield defined preparations of a cell population containing mesenchymal stem cells. Advantageously, isolation of desired cell populations may be performed without the use of centrifugation. In various embodiments, the apparatus may be completely disposable. Cells from the living tissue may include those derived from human tissue and, in particular, adipose tissue. Finally, any of the apparatus embodiments may include a means for cell counting. Various apparatus embodiments may also be useful for isolating cells with negative selection for mononucleated inflammatory cells.

Example 2

Method of Isolation of a Reparative Cell Population from Adipose Tissue

The apparatus of the present invention can be operated by various methods and mechanisms. In one example, the operation of the apparatus can comprise four general steps: (1) introduction of adipose tissue into a digestion chamber; (2) treatment of the tissue in the digestion chamber to separate the constituent viable cells from the bulk tissue by agitation and recirculation through a digestion mesh or filter; (3) phase separation of the digestion mixture based on density in an aqueous solution; (4) collection of desired cell populations without centrifugation. In one embodiment of the invention, a further step is added of passing the digestion mixture through at least one filter prior to phase separation. In another embodiment, the digestion mixture is passed through a series of filters prior to phase separation. In one embodiment the final filter is configured as a dispersing head that separates clumped cells by extrusion within an aqueous media. Optionally, a dispersing filter is utilized prior to the prior to dispersing head to protect the dispersing head from clogging. To illustrate such steps, the operation of the several embodiments of the present invention will now be described in detail. However, Applicants note that one of ordinary skill in the art can use various other methods to operate the apparatus of the present invention.

Figure 5:
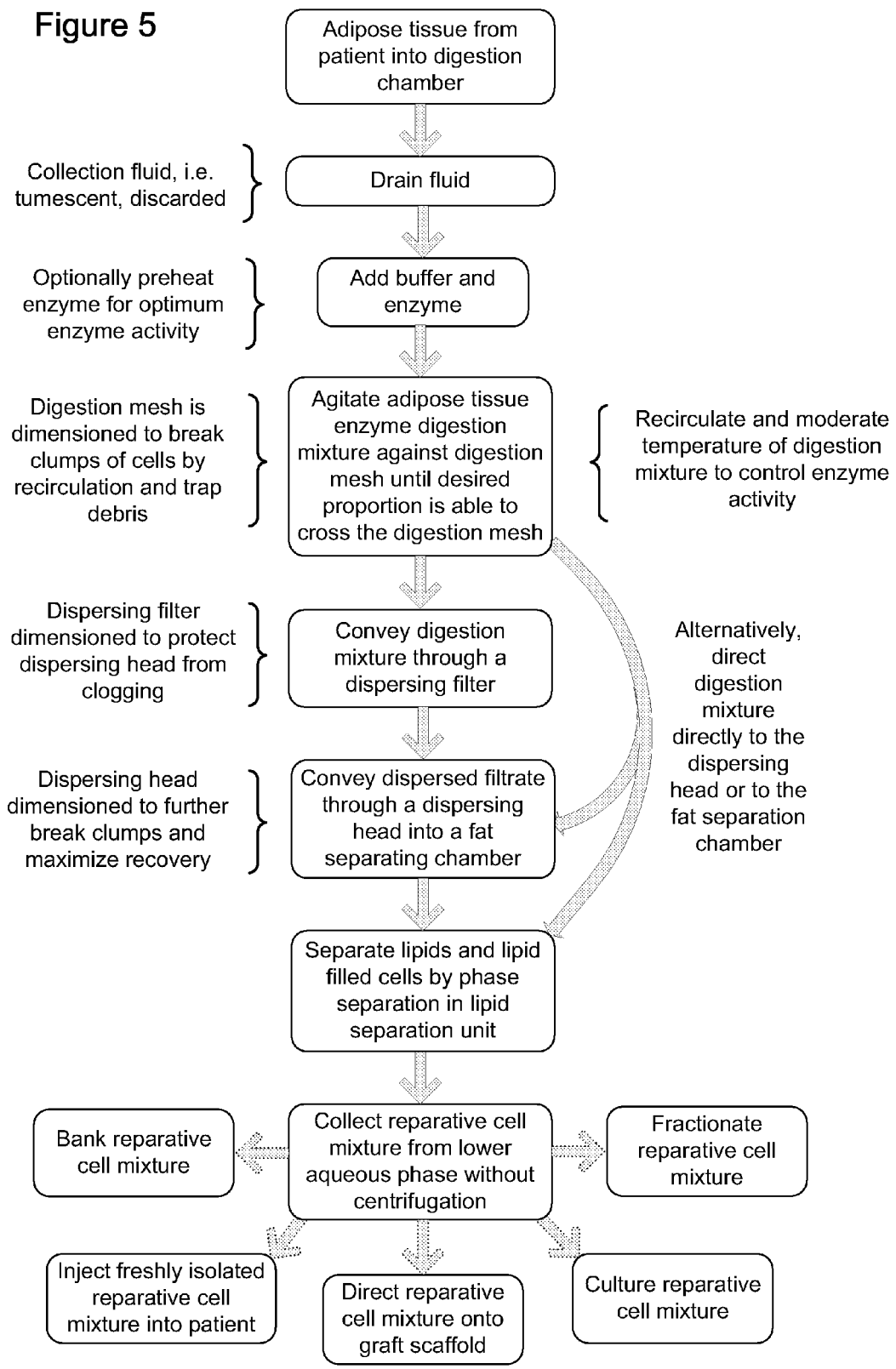
FIG. 5 is a flow diagram of a method of cell isolation from adipose tissue in accordance with one embodiment.

FIG. 5 is a flow chart of one embodiment of an isolation process for obtaining a reparative cell population from adipose tissue according to the invention. As depicted, adipose tissue, typically together with tumescent and/or other fluids is directed into a digestion chamber wherein the tumescent and/or other fluids are drained. Preferably the digestion chamber includes a digestion mesh that divides the digestion chamber into at least two concentric compartments, the outer chamber of which receives the adipose tissue. The adipose tissue is drained of associated fluids which pass through the digestion mesh and can optionally be washed if desired in the chamber by addition of further buffer solutions followed by draining through the digestion mesh.

If desired, a first collection of adipose tissue can be added to the digestion chamber, drained and optionally washed and some or all of the tissue can be collected back out of the apparatus and saved for reinjection of the collected and washed adipose into the patient. A further collection of adipose tissue is then directed into the digestion chamber and, after draining and optionally washing, the further collected adipose tissue is subject to digestion to collect a reparative cell population. As used herein, the term "reparative cell population" refers to the viable non-adipocyte cells of adipose tissue and includes without limitation preadipocytes, mesenchymal stromal cells (MSC), endothelial cells, endothelial progenitor cells, fibroblasts, macrophages and lymphocytes.

The collected adipose tissue is digested to release its constituent reparative cell population, typically by addition of an enzyme solution to the adipose tissue disposed within the digestion chamber. Enzymes that can be introduced into the containers of the present invention generally refer to compounds that can dissociate a biological sample into simpler components. In one example, one or more enzymes may dissociate various cells and fluids from an adipocyte tissue. In another example, one or more enzymes can dissociate specific cell subpopulations from a tissue to form a cellular suspension. Non-limiting examples of enzymes suitable for performing such dissociation can include proteases, collagenase, elastase, dispase, other similar enzymes, and/or mixtures thereof. Such enzymes can be used in pure form or in a mixture and may be obtained as commercially available preparations, such as, for example, the LIBERASE® Blendzyme 1 mixture of collagenases I and II formulated together with dispase as a neutral protease (available from Roche Applied Science, Indianapolis, Ind.).

The temperature of the added enzyme solution can be modified to raise, lower or maximize the activity of the enzyme. In one embodiment the enzyme solution is pre-warmed to a temperature that maximizes enzyme activity without harming the viability of the cells in the tissue to be digested. The adipose tissue together with enzyme solution is agitated. In one embodiment the agitation is provided in part by recirculation across the digestion mesh and through a heat exchanger that adjusts the temperature of the solution as desired for enzyme activity. In other embodiments, the entire apparatus including the digestion chamber is adapted to fit into a rocker assembly that agitates the apparatus during the digestion period. In one embodiment, the rocker assembly is a component of a reusable base unit that includes electronics, pumps, and a heat exchanger for controlling and modifying the temperature of the digestion mixture.

Ultimately, the adipose tissue is broken down by the action of the enzyme together with agitation and recirculation until virtually all of the tissue is in cell clusters small enough to pass through the digestion mesh. The porosity of the mesh is selected based on various desired properties including but not limited to a size sufficient for small clusters of digested tissue to pass through the mesh without rate limiting clogging of the mesh. It is expected that the mesh may act to accumulate and trap certain of the digested connective tissue and other debris while allowing viable cells to pass through as they are released from the tissue. In one embodiment the digestion mesh has a plurality of holes or pores having an opening size of approximately 0.5-2.0 mm. In one embodiment, a digestion mesh having an opening size of approximately 1 mm has been effectively utilized on clinical samples of human adipose tissue.

After a desired quantity of the digested adipose tissue is converted to a digested mixture able to cross the digestion mesh, the digested mixture can be conveyed directly into a fat separation chamber wherein the fat or lipid and lipid containing cells are phase separated from other cells on the basis of their density. Fat is composed of lipid moieties that have a specific gravity significantly less than water. Thus, fat and fat containing cells will float in an aqueous solution, which will have a specific gravity close to that of water (which, as the standard substance against which the relative gravity of other compounds is based, has a specific gravity of 1.0). In contrast, the majority of non-fat containing cells will have a specific gravity close to that of water but will settle due to gravity. After the fat and fat containing cells such as adipocytes have formed an upper layer in the fat separation chamber, the non-fat containing cells are removed via a port at the base of the fat separation chamber. As an important feature of the invention, centrifugation is not necessary to collect the cells although it is appreciated that further processing may optionally include centrifugation among other processes.

Optionally, prior to entering the fat separation chamber, the digestion mixture is subject to one or more additional steps to further separate the various cells in the digestion mixture and maximize the yield. Thus, in one embodiment, the digestion mixture is conveyed through a dispersing head that further breaks clumps and releases non-adipocyte cells that may be trapped in the fat tissue. In one optional embodiment, the dispersing head is configured such that the cells are pumped out of the head in close opposition to a surface that acts to further break clumps of cells. In one embodiment, the dispersing head is generally located proximal to the bottom of the fat separation chamber and is equipped with a plurality of pores. The plurality of pores have a size ranging from about 300 microns to about 1000 microns, in one embodiment and from about 400 microns to about 600 microns in another embodiment. In one particular embodiment used effectively in processing of clinical samples, the average pore size of the dispersing ports is about 500 microns. In another embodiment in which a dispersing head is used, a dispersing filter is placed in-line prior to the fat separating chamber. In one embodiment the dispersing filter is adapted to further divide clumps of cells and to protect the dispersing head from clogging and in one embodiment is dimensioned to have a pore size ranging from about 200 microns to about 300 microns. In yet another embodiment, the dispersing filter has an average pore size of about 265 microns.

In a further alternative embodiment, the digestion mixture is conveyed over a dispersing filter prior to passage through the dispersing head. The intervening dispersing filter acts to further dissociate cell clumps and protects the dispersing head from clogging.

After separation, the reparative cell population is removed from the lower aqueous phase of the fat separation chamber and is used as desired including direct use by reinjection into the patient, potentially after placement on a graft scaffold, or the reparative cell population may be subject to further purification, cell culture, and/or cell banking.

Example 3

Further Apparatus Embodiments

Figure 6:
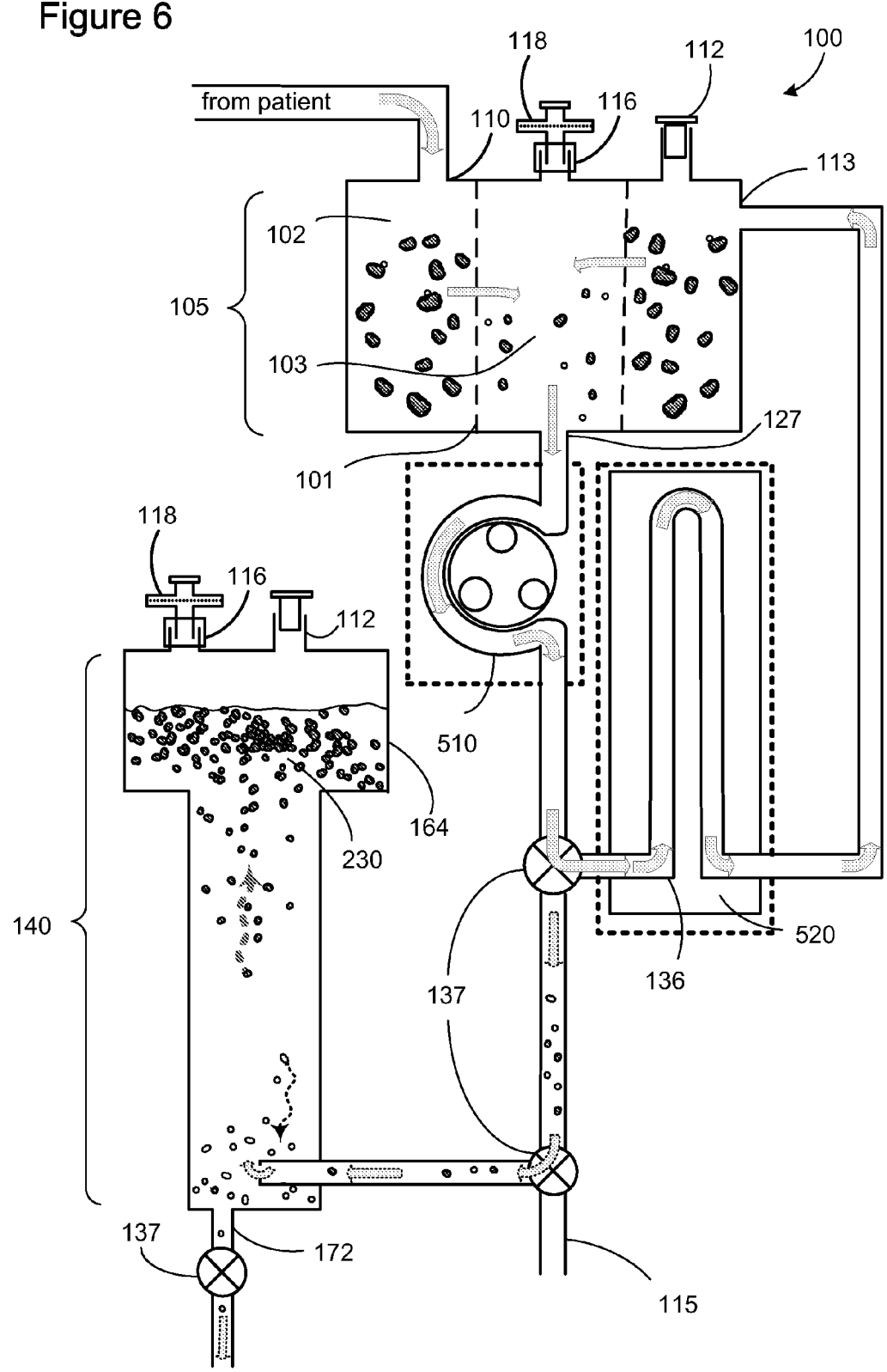
FIG. 6 is a diagram of one embodiment of a cell separation apparatus.

FIG. 6 is a schematic depiction of one embodiment of the present invention. Apparatus 100 includes a digestion chamber 105 and a fat separation chamber (a.k.a. lipid separation unit) 140. Digestion chamber 105 generally refers to a housing that can receive and treat a biological sample and can have various shapes and structures. The depicted digestion chamber 105 includes at least two compartments, predigestion chamber 102 and post digestion chamber 103, separated by digestion mesh 101. The digestion chamber may optionally include a vent 116 that may include a filter 118 to preserve sterility such as, for example, an ACRODISC brand syringe filter (Pall Scientific).

In one embodiment of the invention, the cell isolation apparatus may include a dedicated port, such as for example a dip port, for removal of lipoaspirate or washed lipoaspirate from the predigestion chamber for use in autologous fat grafting. Alternatively, the lipoaspirate may be removed through an existing port having other functions. Where the port is located on an upper surface of the digestion chamber, the lipoaspirate may be removed with an inserted conduit such as a cannula. Alternatively, the port may be located on a lower aspect and the lipoaspirate removed by drainage or pumping directly from the port.

In the depicted embodiment, the digestion chamber 105 is cylindrical and the pre and post digestion chambers are formed by placement of an inner mesh cylinder 101 disposed within the digestion chamber. The porosity of the mesh is selected based on various desired properties including but not limited to a size sufficient for small clusters of digested tissue to pass through the mesh without rate limiting clogging of the mesh. In one embodiment the digestion mesh has a plurality of holes or pores having an opening size of approximately 2-0.5 mm. In one embodiment found to be effective, the mesh is a polypropylene mesh having an average pore size of approximately 1 mm.

Adipose tissue in extraction fluid or tumescent is introduced via entry port 110 into predigestion chamber 102. The extraction fluid or tumescent is able to drain through mesh 101 and out drain port 127 and ultimately to waste port 115 for discard. Valves 137 and/or clamps (not shown) control the pattern of flow, as well as the action of pump 510. After draining of the extraction fluid and optional washing if desired, a digestion buffer is added to the predigestion chamber via a fill port such as fill port 112 and a digestion enzyme or cocktail of enzymes is added to the predigestion chamber. The enzyme can be added together with the digestion buffer if desired. In one embodiment found to be effective, the buffer solution utilized was a lactated Ringer's solution, however other physiologic buffers are suitable and are readily envisioned by one of skill in the art. In the depicted embodiment, the enzyme may be added through a dedicated port such as fill port 112, which may be constructed in any number of ways including for example as a valvable opening or as a self-sealing septum. Optionally, a poloxamer may be added to improve flow and as an aid in maintaining cell viability. For example, poloxamer 188 may be used at concentrations ranging from about 0.05% (w/v) to about 5% (w/v).

Figure 13:
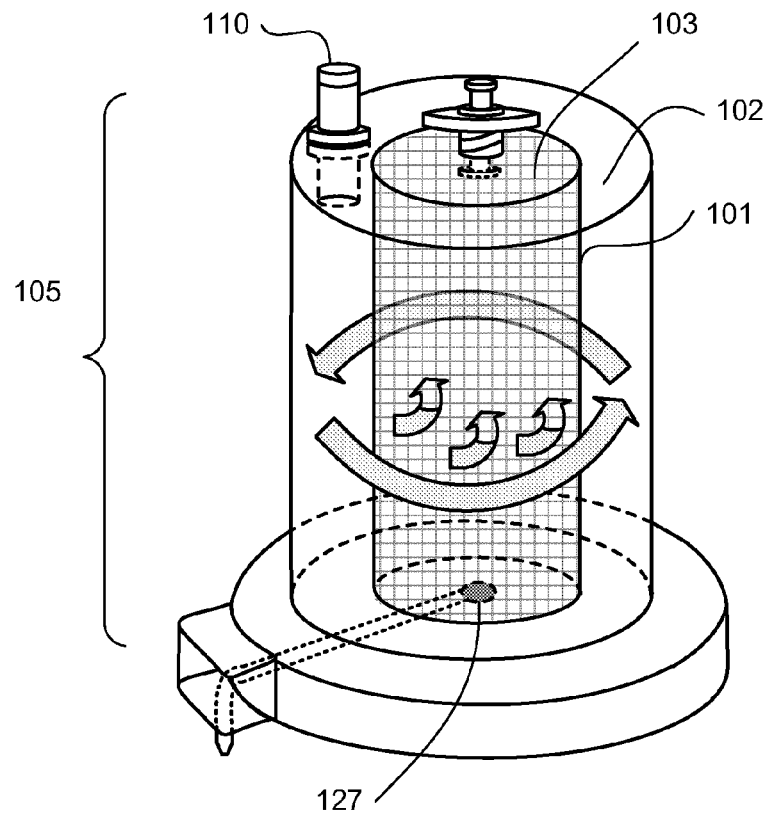
FIG. 13 is a three dimensional depiction of a digestion chamber according to one embodiment of the invention.

A digestion period is then begun wherein the digestion mixture is recirculated, typically through the action of a pump such as for example roller or peristaltic pump 510. The direction of flow is from predigestion chamber 102 across digestion mesh 101, into post digestion chamber 103, out drain port 127, and back around into the predigestion chamber through recirculation port 113. A three-dimensional view of one such embodiment is presented in FIG. 13 where as depicted, the predigestion chamber surrounds the inner post digestion chamber. This configuration provides ample volume for both chambers and, as can be seen by the depicted arrows, the digestion mixture is able to circulate around as well as through the digestion mesh 101.

As part of the recirculation loop the digestion mixture may be passed through a heat exchanger loop 136 by the action of pump 510. In a preferred embodiment, equipment such as pump 510 and heating element 520, shown surrounded by dashed lines, are adapted to be operably attached to apparatus 100 via tubing but are part of a reusable base unit that constitutes capital equipment in contrast to apparatus 100 which is designed for clinical use to be a disposable unit that does not require any electrically operable components and can be supplied as a presterilized single use unit. The heat exchanger loop 136 is heated by heating element 520 which provides controlled heating to the heat exchanger loop for optimum enzyme activity. As digestion continues an increasing greater proportion of the adipose tissue is able to cross the digestion mesh 101. In a preferred embodiment, the apparatus 100 is agitated by shaking during the digestion period. After the adipose tissue is sufficiently digested, the recirculation loop is ceased and the digestion mixture is directed to fat or lipid separation unit 140.

In one embodiment, prior to allowing the digestion mixture to enter the lipid separating unit, the unit is prefilled with a separation buffer. In further embodiments of the present invention, various compositions may be introduced into a lipid separating unit to aid in phase separation. For instance, the separation buffer may comprise separation facilitating compounds that may be introduced into lipid separating unit 140.

The separation buffer may be added through various mechanisms. In the depicted embodiment, a fill port 112 is provided for separation buffer addition. In the lipid separation unit 140, phase separation occurs and the lipid and lipid containing cells float up through the separation buffer as depicted by the upward directed thick dashed arrow and ultimately form a floating lipid phase 230. The non-lipid containing cells, including a reparative cell population, settle down as depicted by thin downward directed dashed arrow. After a desired period wherein the lipids have had time to migrate to the top of the chamber, the underlying phase is removed via collection port 172. In further embodiments, lipid separating unit 140 could alternatively be equipped with a means to detect the interface between the aqueous phase and the lipid phase. This detection means may rely on a colorimetric determination or by monitoring changes in density, for example. If desired, after removal of the desired cells and draining of the apparatus, the entire cycle can be repeated by addition of fresh adipose tissue to the digestion chamber and re-addition of fresh digestion buffer.

Figure 7:
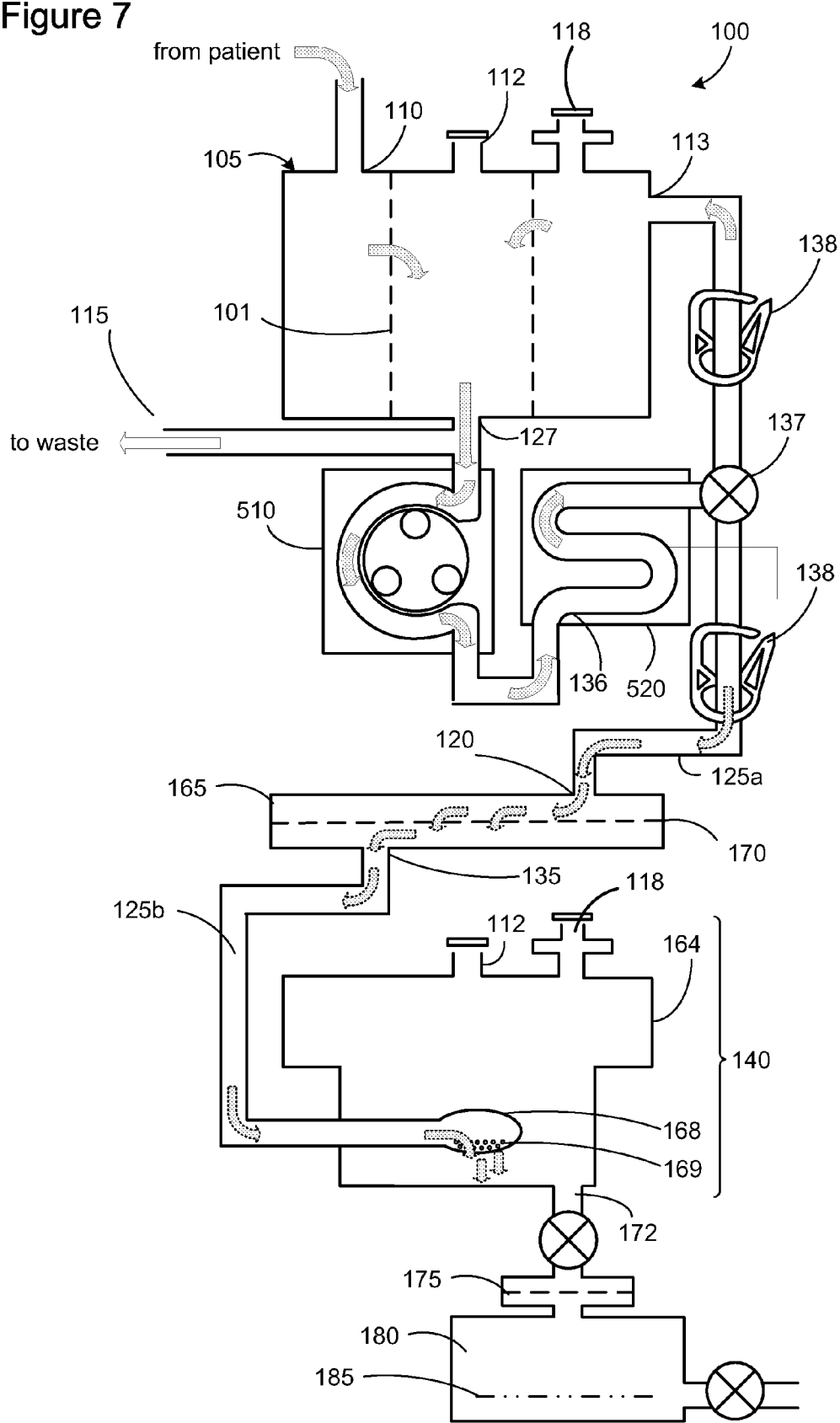
FIG. 7 is a diagram of an alternative embodiment of a cell separation apparatus, including an optional cell seeding chamber.

In an alternative embodiment provided in FIG. 7 flow patterns are depicted with the recirculation of tissue during digestion depicted in solid lined arrows while the digested mixture is depicted in dashed lined arrows. In the depicted embodiment, apparatus 100 further includes a dispersing head 168 having a plurality of pores 169 as the entry port of fat or lipid separating chamber 140. In one embodiment, the average pore size of the dispersing head is in the range of about 0.3 mm (300 microns) to about 1 mm (1000 microns), while in another embodiment the average pore size is from about 0.4 mm (400 microns) to about 0.6 mm (600 microns). In one embodiment, the dispersing head has an average pore size of about 0.5 mm (500 microns).

Figure 11:
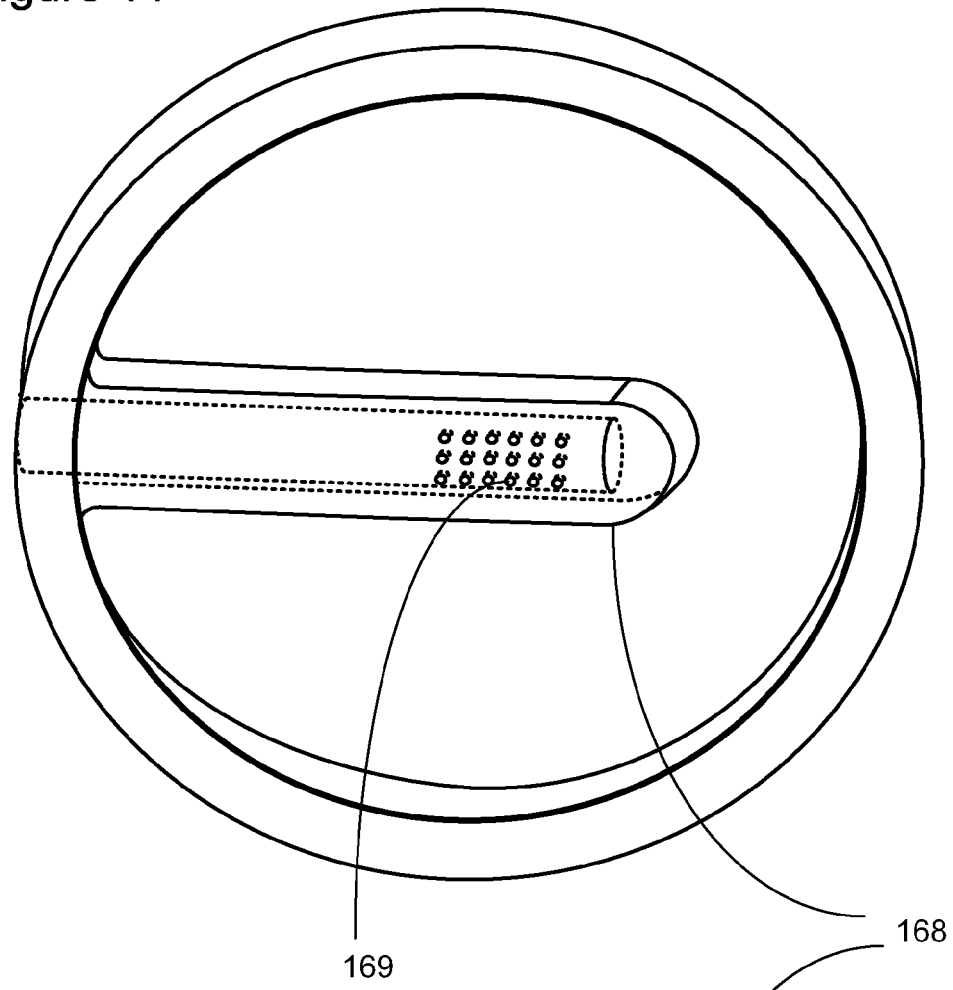
FIGS. 11 and 12 provide close-up views of an embodiment of a dispersing head for use in the fat or lipid separating unit of the invention.
Figure 12:
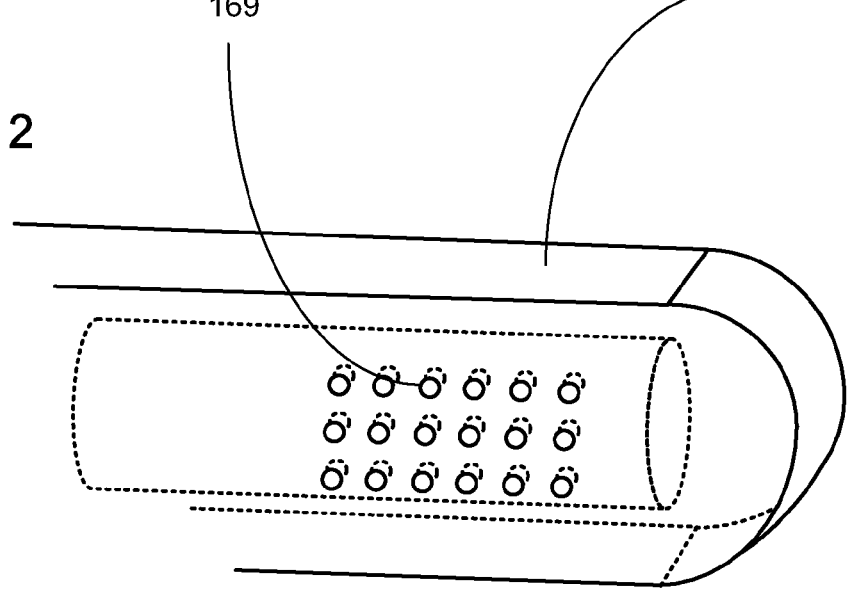

In the depicted embodiment of FIG. 7, dispersing head 168 is a substantially rigid structure designed to be located relatively close to the bottom of the lipid separating unit 140. As depicted, the dispersing head can be directed with its exit openings or pores 169 facing downward such that the fluid flow entering lipid separating unit 140 is in the opposite direction of the buoyancy of lipid-filled cells and thus further reduces clumps and releases reparative cells trapped together with lipid-filled adipose cells. Use of the dispersing head has been shown by the present inventors to result in greater yield of reparative cells. One embodiment of a dispersing head 168 including 0.5 mm dispersing pores 169 is shown in detail in FIGS. 11 and 12.

Figure 8:
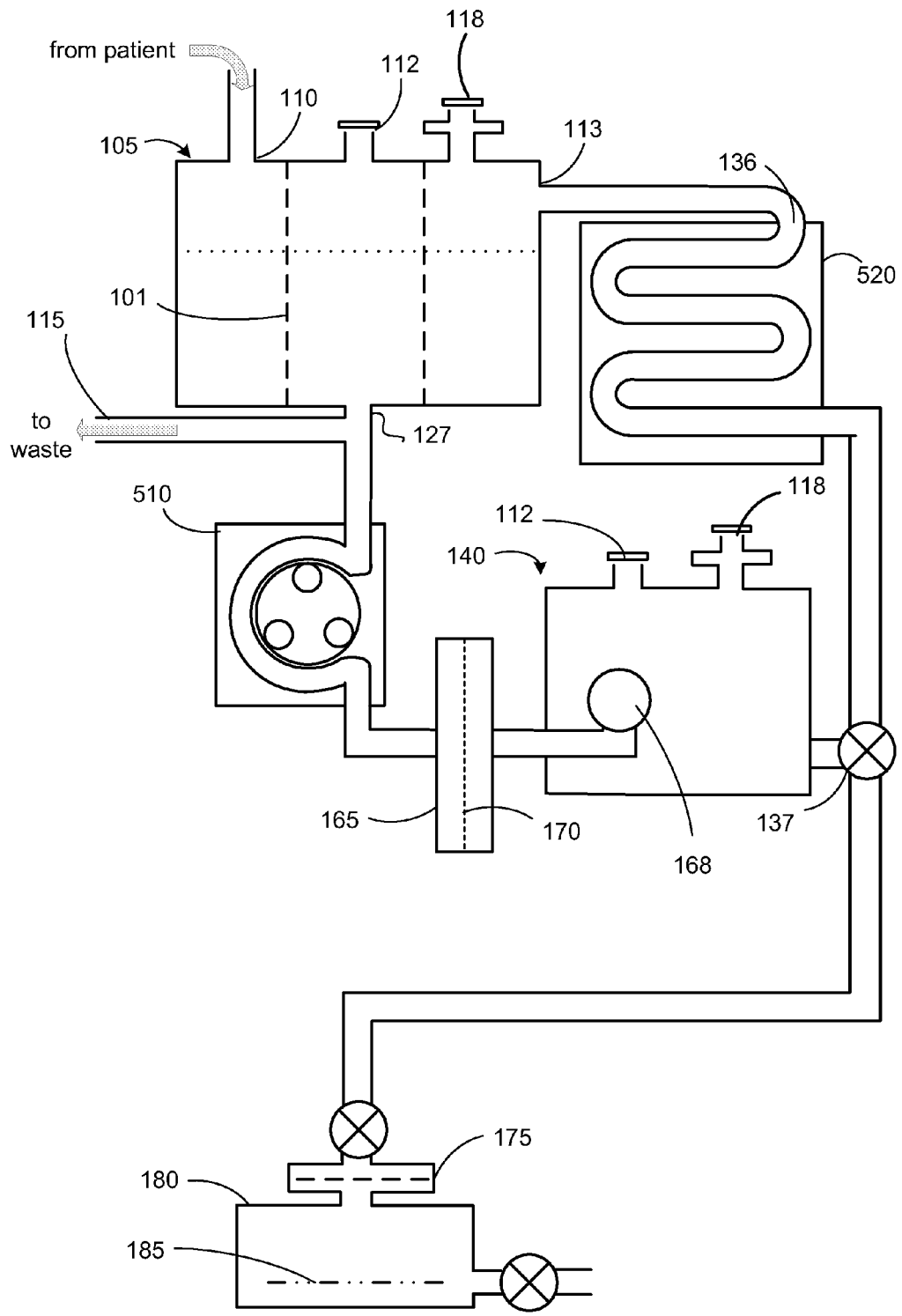
FIG. 8 is a diagram of an alternative embodiment of a cell separation apparatus.

In the embodiment depicted in FIGS. 7 and 8, a further dispersing filter chamber 165 including dispersing filter 170 is included in-line prior to the dispersing head 168 and is adapted to further divide clumps of cells and to protect the dispersing head from clogging. In one embodiment, the dispersing filter is dimensioned to have a pore size ranging from about 0.2 mm (200 microns) to about 0.3 mm (300 microns). In yet another embodiment, the dispersing filter has an average pore size of about 0.265 mm (265 microns). However, one of ordinary skill in the art will recognize other suitable filter sizes that can be used in the present invention. Furthermore, one of ordinary skill in the art will recognize that dispersing filter 170 can be in other forms or may, in some embodiments, be eliminated entirely depending on the configuration of the apparatus.

Likewise, one of ordinary skill in the art will recognize that container 105 can have various other shapes and arrangements. As with other embodiments, digestion chamber 105 is in fluid communication with the lipid separating unit 140, and any intervening filters, via a tubing network as shown in FIGS. 6-10. The pattern of flow is controlled by one or more valves 137 and/or clamps 138 as well as the action of the pump 510. The embodiment depicted in FIG. 7 includes a separate waste line 115.

Figure 9:
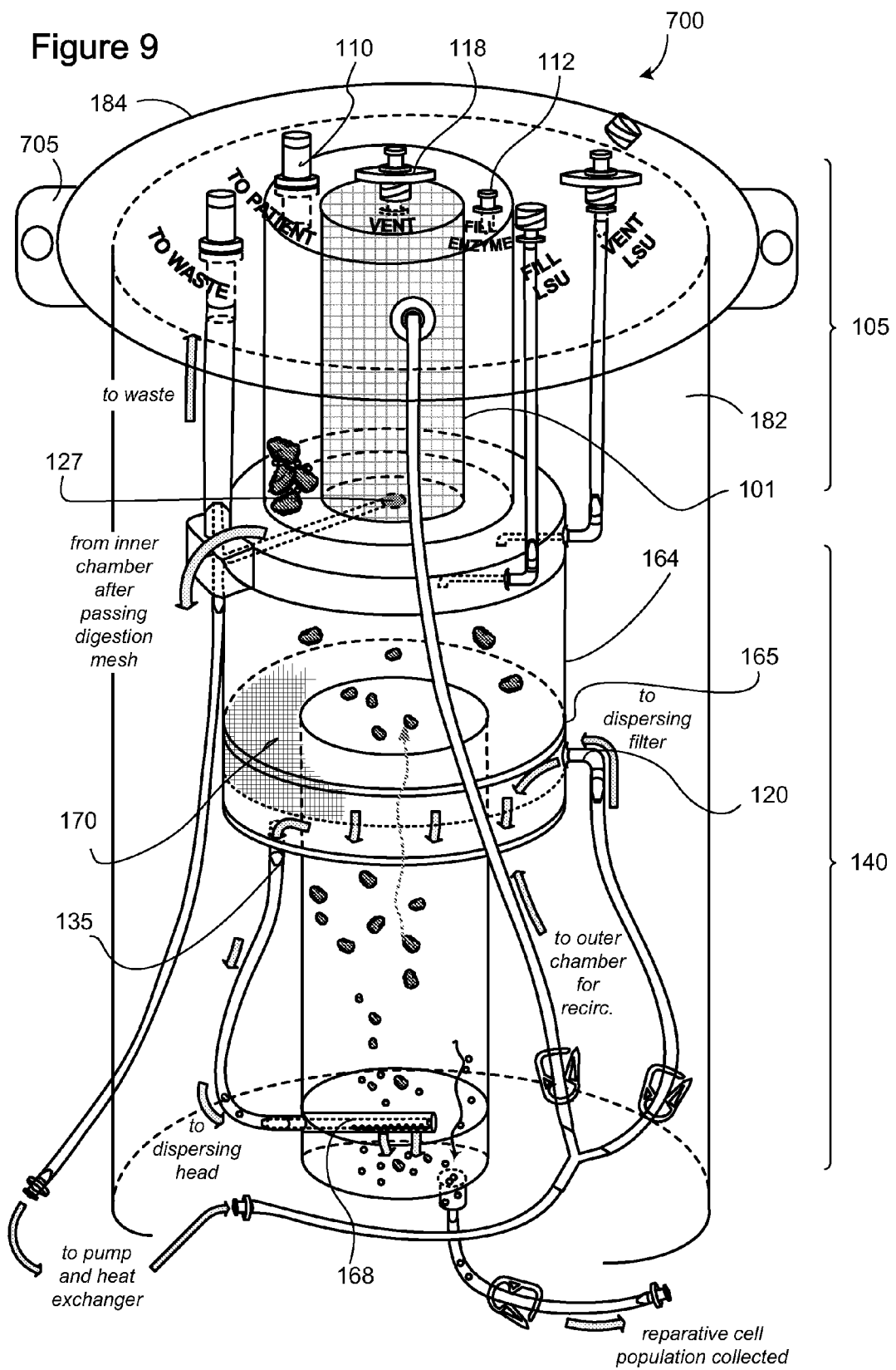
FIG. 9 is a three dimensional view of an alternative embodiment of a cell separation apparatus for isolation of cells from adipose tissue.

As depicted in FIGS. 6, 7 and 9, the upper most portion 164 of the lipid separating unit may have a greater diameter than the lower portion to accommodate the floating fat layer. The embodiment depicted in FIGS. 7 and 8 also includes an optional cell seeding chamber 180, which may include a cell seeding substrate or scaffold 185. Such a seeding chamber may serve various functions. In one embodiment, the chamber can contain the aforementioned substrate or scaffold on which cells might be seeded as liquid is drained from the lipid separating unit. In operation, reparative cells collected using the apparatus can be directly disposed onto the cell seeding substrate and either implanted on the patient or removed to an incubator for further cellular expansion. In another embodiment, the chamber might allow buffer exchange. In further embodiments of the present invention, chamber 180 may be entirely absent. In some of such embodiments, lipid separating unit 140 may have a port and/or an opening for passage of separated material.

In another embodiment, various chamber and compartment of the apparatus might contain materials such as antibodies or aptamers or thioaptamers that could be used to negatively select for materials to be removed from the processed material for further purification. Cell selection agents that may be introduced into containers of the present invention generally refer to one or more compounds for positive cell selection or negative cell selection. For negative cell selection, such cell selection agents may aid in the depletion of various cells from a biological sample, such as the depletion of leukocytes and/or erythrocytes in one embodiment. For positive cell selection, the cell selection agents may specifically bind a desired cell type for isolation. Cell selection agents suitable for use in the present invention may include, without limitation, an antibody (see U.S. Pat. Nos. 6,491,918, 6,482,926, 6,342,344, 6,306,575, 6,117,985, 5,877,299, and 5,837,539), an aptamer (see U.S. Pat. No. 5,756,291), and/or a thioaptamer (see U.S. Pat. No. 6,867,289), for example, all of which are incorporated herein by reference in their entirety. In some embodiments, the cell selection agents may be immobilized on polymer beads, for example, and placed in digestion chamber 105 through port 112. The cell selection agents may also be immobilized on the inner surface of various portion of the apparatus itself such as for example digestion container 105, digestion mesh 101, dispersing filter 170, cell collecting filter 175, etc. The agents could also be placed on a matrix, or on a scaffold.

As depicted in FIGS. 6, 7 and 8, the lipid separating unit may optionally include fill port 112 and a vent port 116 with sterility filter 118. As depicted in FIGS. 7 and 8, an additional collected cell filter 175 may be optionally included prior to the seeding chamber 180. An included collected cell filter may optionally provide for purification and sizing of desired cells as well as prevent clogging of down-stream components. Collected cell filter 175 is generally a circular structure in the present example, though a person of ordinary skill in the art could envision other shapes and structures.

In the example shown in FIGS. 7 and 8, collected cell filter 175 is desirably a filter with a pore size of less than about 250 microns. However, in other embodiments, collected cell filter 175 can have a pore size ranging from about 0.01 mm (10 microns) to about 0.1 mm (100 microns). In another embodiment, collected cell filter 175 can have a pore size ranging from about 0.03 mm (30 microns) to about 0.05 mm (50 microns). In a further embodiment, the average pore size in collected cell filter 175 is about 0.037 mm (37 microns). In additional embodiments, the collected cell filter may be entirely absent.

FIG. 9 depicts one embodiment of a working prototype cell separator apparatus 700 that has been effectively utilized in separation of reparative cell populations from human adipose tissue. The depicted apparatus 700 for isolating cells from adipose tissue includes a digestion chamber 105 having at least one inlet port 110 and at least one outlet port 127 and adapted for separation of adipose tissue across a digestion mesh 101 during enzymatic dissociation of the adipose tissue into a dissociated cell mixture; a dispersing filter 170 having an inlet port 120 and an outlet port 135 and in fluid communication with the digestion chamber and configured to filter the dissociated cell mixture into a dispersed cell mixture; and a lipid separating unit 140 including at least one dispersing head 168 having a plurality of pores in fluid communication with an outlet port of the dispersing filter, wherein lipid separating unit is adapted for fluid phase separation of lipids and adipocytes from the dispersed cell mixture.

In one embodiment, digestion mesh has a pore size between 500 to 1500 microns and the dispersing filter has a pore size of about 200 to 500 microns. In one particular embodiment, the digestion mesh has a pore size of about 1000 microns, the dispersing filter has a pore size of about 265 microns and the dispersing head has dispersing pores of about 500 microns. In one particular embodiment such as that depicted in FIG. 9, the digestion chamber, dispersing filter and lipid separating unit are in a fixed integrated columnar arrangement and a filtering surface orientation of the digestion mesh is essentially perpendicular to a filtering surface orientation of the dispersing filter. The apparatus depicted in FIG. 9 can be disposable and supplied sterile and is operable in a closed manner to maintain sterility. As depicted in the embodiment of FIG. 9, the apparatus includes a lipid separating unit adapted to provide a vertical column for a fluid phase separation of a plurality of individual cells within the cell mixture based on density of the individual cells; and at least one dispersing head having a plurality of pores disposed proximally to a bottom inner surface of the lipid separating unit and adapted for forcibly flowing the cell mixture against an inner surface within the lipid separating unit and thereby disrupting cell clusters within the cell mixture prior to fluid phase separation.

In the embodiment depicted in FIG. 9, the apparatus includes an outer protective cylinder 182 which houses the digestion chamber 105 and the lipid separating chamber 140. A top plate 184 is attached to cylinder 182 and provides access to the interior of the unit through a plurality of labeled ports including inlet port 110, vent 118, fill port 112 as indicated. In the depicted embodiment, top plate 184 includes attachment wings 705 for connecting to an agitator mechanism (not shown in FIG. 9). In the depicted embodiment, the bottom of the digestion chamber effectively forms an upper portion 164 of the lipid separating unit. Dispersing filter chamber 165 including dispersing filter 170 is disposed around the outer perimeter of an upper aspect of the lipid separating unit and effectively forms the base of the upper enlarged portion 164 of the lipid separating chamber 140. Some or all of the ports may be capped, including with a sterile filter, in order to keep the inner chambers sterile.

Figure 10:
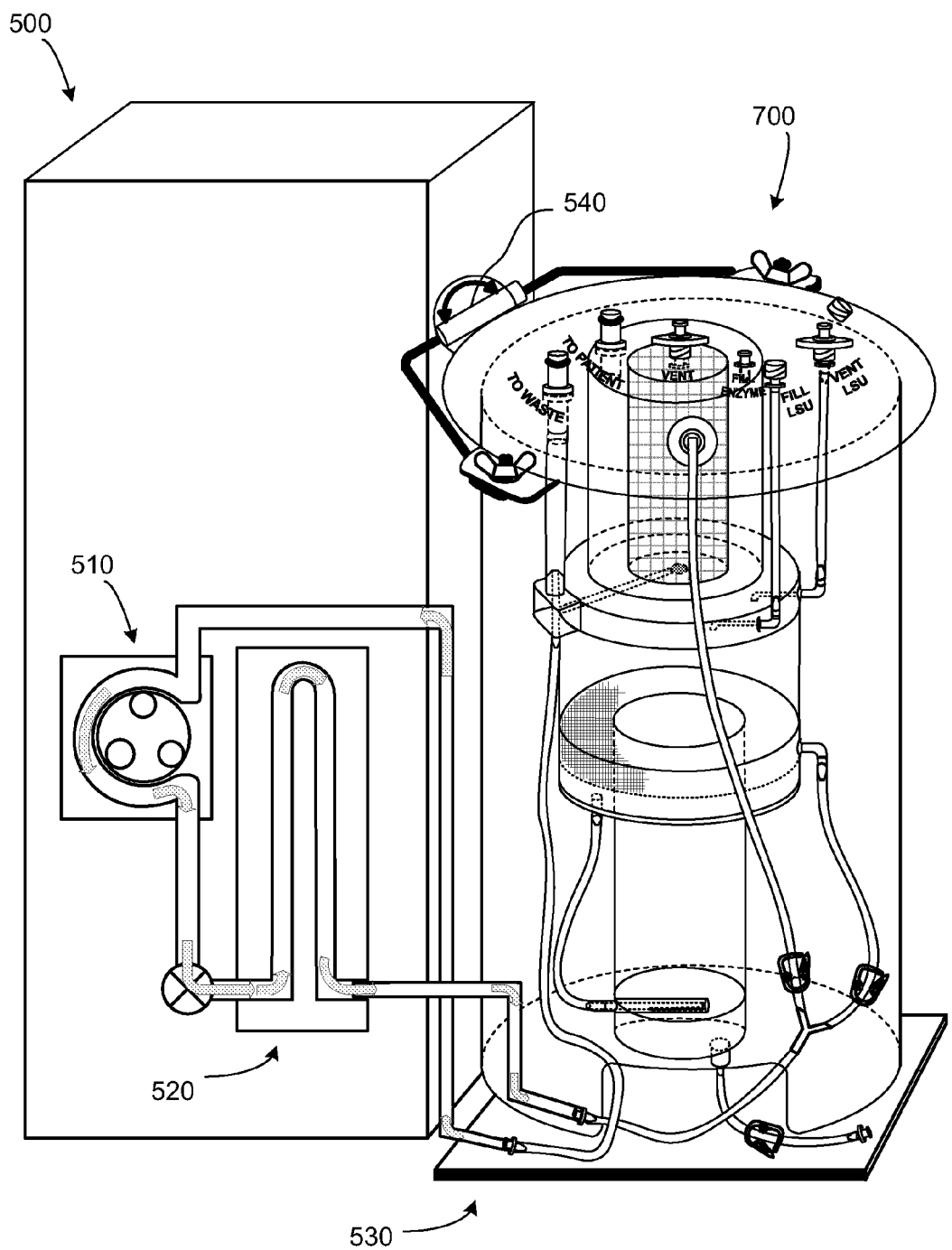
FIG. 10 is a three dimensional view of the embodiment of FIG. 9 including a base station that includes a pump, heat exchanger and agitation device.

In various embodiments, the apparatus of the present invention is associated with a heating-agitation device to aid in the treatment of biological samples. For instance, as depicted in FIG. 10, apparatus 700 can be associated with a base unit 500 that houses pump 510, heating unit 520 and agitation device 540. In the depicted embodiment, the agitation device includes platform 530 on which apparatus 700 rests, although other means of holding and shaking apparatus 700 can be envisioned. Furthermore, base unit 500 will house necessary switches and read-out gauges.

Figure 14:
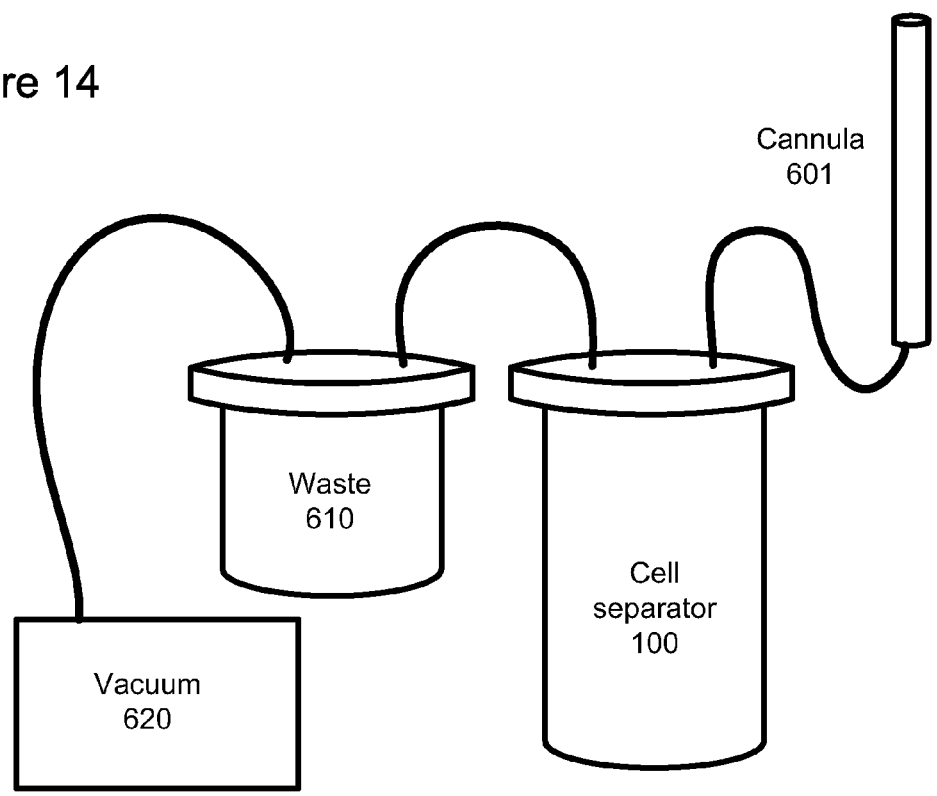
FIG. 14 is a figurative depiction of a vacuum system for aspiration of adipose tissue into the digestion chamber using a common cosmetic surgery setup.

As depicted in FIG. 14, various embodiments of the present invention can also be associated with a cannula 601, waste container 610, and vacuum source 620 for providing the motive force for collecting and introducing a biological sample into the cell separator apparatus 100.

In practice and in one embodiment, the collected biological sample is disposed into digestion chamber 105 by the action of vacuum source 620. Apparatus 700 including digestion chamber 105 may be heated and agitated by the utilization of the heating and agitation capabilities of base unit 500 shown in FIG. 10. In one embodiment, apparatus 700 may be disconnected from vacuum source 620 and immobilized onto agitator 540. Portions of tubing that form the sterile fluid flow conduits of apparatus 700 can then be operably connected to pump 510 and heating block 520. Valves or clamps directing fluid flow into the recirculation loop through the digestion chamber are set. As a result, the biological sample in container 105, while being agitated, travels through the recirculation loop, including through the heat exchanger disposed on heater 520 and back into container 105. The digestion mesh of container 105 continuously filters the dissociated components of the biological sample during this process. Such agitation, heating, filtration and re-circulation can desirably proceed for an extended period of time, such as from about 20 to 60 minutes.

Following the recirculation digestion period, the separation of the biological sample into an aqueous bottom layer with cells and a top lipid layer can occur by changing the valves and/or clamps to direct the flow of the digestion mixture through the dispersing filter 170 of dispersing chamber 165 and on to the lipid separating unit 140 wherein the dispersed digestion mixture is further separated through the dispersing head at the bottom of the lipid separating unit. The dispersed digested mixture is allowed to remain in the lipid separating unit at room temperature for about 5 to 30 minutes. Without being bound by theory, such a separation occurs because lipids, including lipid-filled cells, have a lower specific gravity and therefore float to a top layer, whereas the aqueous layer, which includes non-lipid filled cells and other dense materials, settle to the bottom. The collection of isolated cells in the aqueous bottom layer of a lipid separating unit can also be achieved by various means. For instance, in lipid separating unit 140, a lower clamp or valve can be released such that the aqueous bottom layer with isolated cells flows from outlet 172. The cells may then be collected and used for various purposes.

Example 4

In one example, a reparative cell population was isolated as follows. Lipoaspirate was collected under informed consent in the operating room directly into a unitary purification apparatus such as that depicted in FIGS. 9 and 10 by standard suction assisted lipoplasty with tumescent. The apparatus including lipoaspirate and residual tumescent fill was transported to the laboratory and processed within 2 hours of collection. In practice however, it is anticipated that the purification apparatus will be suitable for, and will be used, in the operating suite. The digestion chamber of the apparatus as depicted in FIG. 10 included a predigestion chamber and a postdigestion chamber separated by a nylon mesh having a pore size of approximately 1 mm. The tumescent was drained and a volume of approximately 100 ml of lactated Ringer's, which was prewarmed to 37° C. and contained a proteolytic enzyme combination comprised of collagenase IV (60,000 U) and dispase (120 U), was added to the lipoaspirate. An additional 150 ml of lactated Ringer's was added to the lipid separating unit. The digestion recirculation loop was implemented by a pump actuated flow path from the predigestion chamber into the postdigestion chamber and including passage across a heat exchanger that maintains the digestion mixture at approximately 37° C. Recirculation was continued for approximately 30 to about 60 minutes or until greater than 90% of the cellular volume of the predigestion chamber was able to pass the 1 mm mesh into the post digestion chamber. The design of the pre and post digestion chambers, separated by the nylon mesh across which the recirculation flow path passes repeatedly, provided trapping of connective and other debris tissue on the digestion mesh.

After digestion was sufficiently complete, the digestion mixture was pumped tangentially over a nylon dispersing filter having a pore size of 250 μm. The filtered digestion mixture was then pumped into a columnar lipid separating chamber that was integral to the apparatus. As previously mentioned, the lipid separating chamber was prefilled with a volume of 150 ml lactated Ringer's solution prior to introduction of the digestion mixture such that when the filtered digestion mixture entered the chamber, any clusters of cells including lipids or adipocytes, were subject to fluid shear as the lipid moieties float upward in the aqueous solution. The filtered digestion mixture entered the lipid separating chamber through a dispersing head having a plurality of downwardly directed pores with a pore size of 500 μm and disposed proximally to a bottom inner surface of the lipid separating unit. The design was adapted for forcibly flowing the cell mixture against an inner surface within the lipid separating unit and thereby further disrupting cell clusters within the cell mixture prior to fluid phase separation. Fluid phase separation was allowed to proceed at room temperature for about 5 to about 30 minutes prior to collection of the stromal vascular fraction from the bottom of the lipid separating chamber.

After processing tissue in the device, cell viability and cell number were determined. In one processing run, the collected cells were plated at a density of approximately $7 \times 10^5$ cells/$cm^2$ into a T185 flask in MEM, 20% (v/v) FBS including and antibiotic/antimycotic and cultured overnight at 37° C. in a humidified 95% O2, 5% CO2 atmosphere. After overnight, non-adherent cells were harvested by aspiration, and adherent cells were harvested by trypsinization. Immediately after harvest, cells were processed for flow cytometry. Numbers represent the net percentage positive cells after subtraction of background (2' Ab only) and gating to remove debris. FIGS. 15A and B represent data from two processing runs. Cells collected as described in Example 4 have also been characterized by direct analysis without separation into adherent and non-adherent populations. The results are depicted in FIG. 15C.

In comparing the cells isolated as disclosed herein with mesenchymal stromal cells isolated using centrifugation and plastic adherence in accordance with conventional preparation methods, several notable differences are apparent. Mesenchymal stromal cells have been classically isolated from adipose tissue using enzymatic digestion, centrifugation to remove lipid filled cells and plastic adherence with culture in vitro. These cells show a fibroblast-like morphology. Although the cells are initially heterogeneous, the phenotype of population changes in culture including loss of CD31+, CD34+, CD45+ cells, and an increase in CD105 and other cell adhesion type molecules. Generally, ≦10% of the cells express markers associated with stemness (e.g., CXCR4, sca-1, SSEA-4) and a substantial fraction differentiates into adipocytes in inductive media. A lesser fraction differentiates into other lineages (bone, cartilage, nerve) in inductive media.

The reparative cell population isolated as disclosed herein without centrifugation or plastic adherence is also a heterogenous population and generally ≦10% express markers associated with stemness (e.g., CXCR4, Sca-1, SSEA-1, SSEA-4, VEGFr2, CD117, CD146, Oct4). However, a substantial fraction of the early multipotent stem cells are not plastic adherent. Importantly, a substantial fraction of cells expressing markers of stemness, endothelial cell lineages and/or exhibiting a small diameter (≦6 mm) are not adherent and are lost using conventional isolation methods that rely on plastic adherence or centrifugation.

Figure 16:
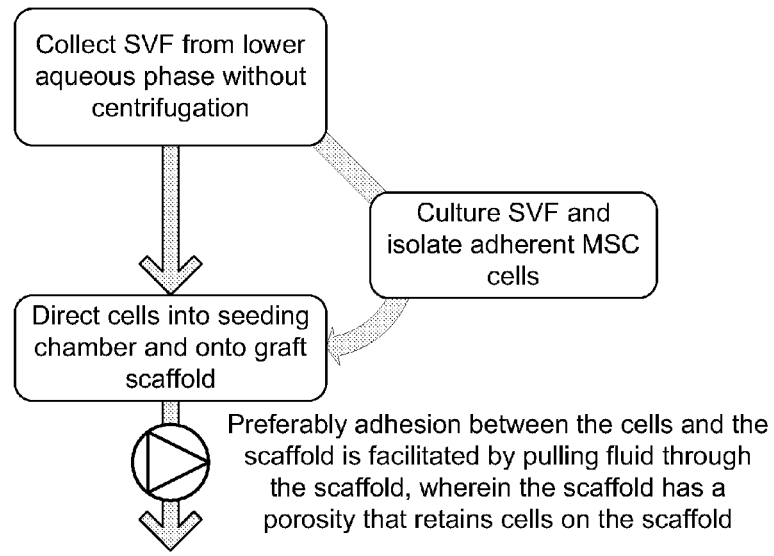
FIGS. 16 and 17 are flow charts depicting cells seeding methods according to two embodiments of the invention.

Seeding chambers: In certain embodiments of the invention, a cell seeding chamber is utilized together with the cell isolation apparatus. For example, as depicted in FIG. 16, procedural steps in use of a seeding chamber may include the following: SVF or MSC are conveyed to a seeding chamber which is adapted for use depending on a configuration and cell selection criteria tailored to the tissue to be repaired. The cells may be introduced into the seeding chamber in a way that promotes or even forces physical interaction between the cells and the matrix material of the scaffold including through use of a partial vacuum, pressure, or other physical force applied to the cells to force the cells into physical contact with the matrix or scaffold. For example, in one embodiment of the invention, introduction of the reparative cells onto the scaffold is facilitated by pulling the cells through a porous scaffold to promote physical contact between the cells and the surface of the scaffold. After a certain contact time is allowed for desired cells to attach and/or migrate into structure of the scaffold, cells that have not adhered to the scaffold may be evacuated or washed from the seeding chamber if desired. For use, the scaffold is removed from the seeding chamber and applied to or implanted at the target site on a human or animal patient.

Figure 17:
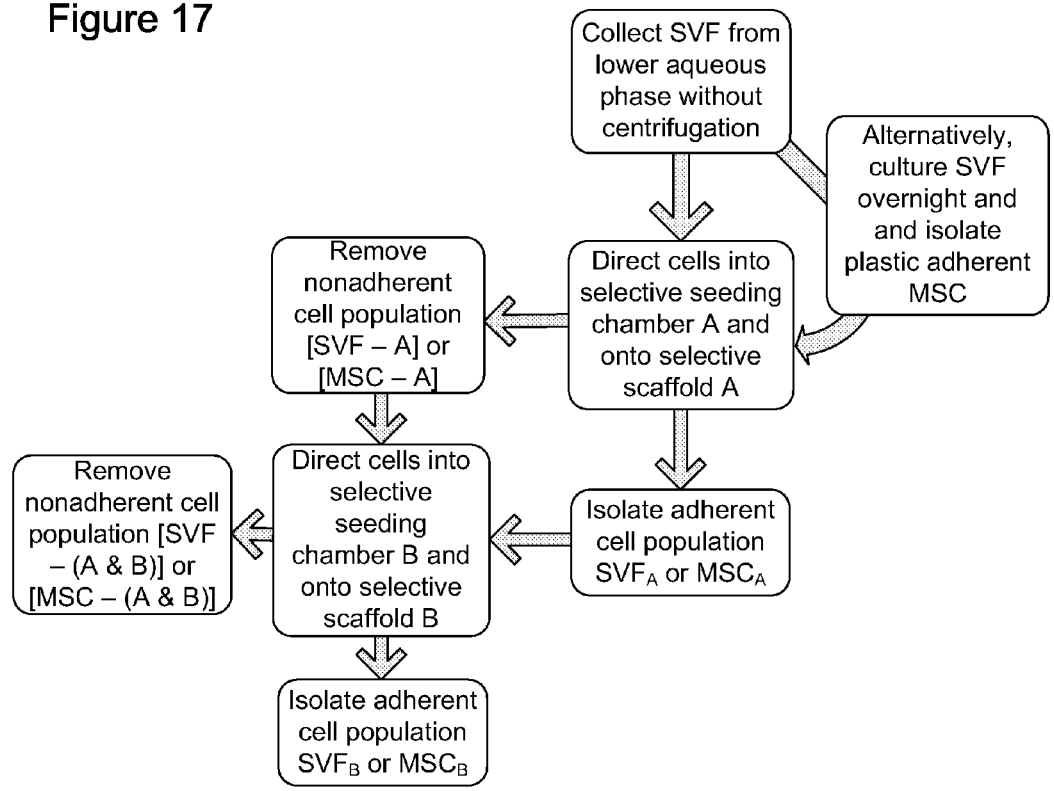

In an alternative embodiment as depicted in FIG. 17, a series of selective seeding chambers are utilized in serial fashion. For example, SVF cells are isolated and directed into selective seeding chamber A wherein scaffold A is adapted to selectively bind a population of cells on the basis of an "A" ligand. Non-adherent cells lacking the "A" ligand are washed from the A chamber and directed to selective seeding chamber B, which contains selective scaffold B, which is adapted to selectively bind a population of cells on the basis of a "B" ligand. Non-adherent cells lacking both the "A" and "B" ligand are washed from chamber B and collected. Adherent cells in chambers A and/or B may be collected after release from the scaffolds. The selective seeding chambers may be used for either positive or negative selection in the generation of specific cell populations.

Figure 18A:
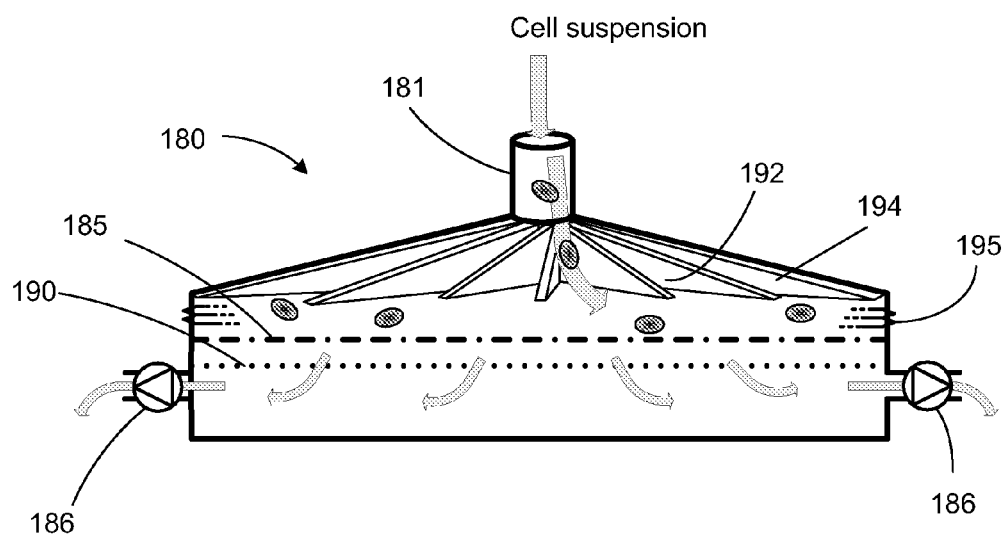
FIGS. 18A and B represent two alternative embodiments of cell seeding chambers.
Figure 19:
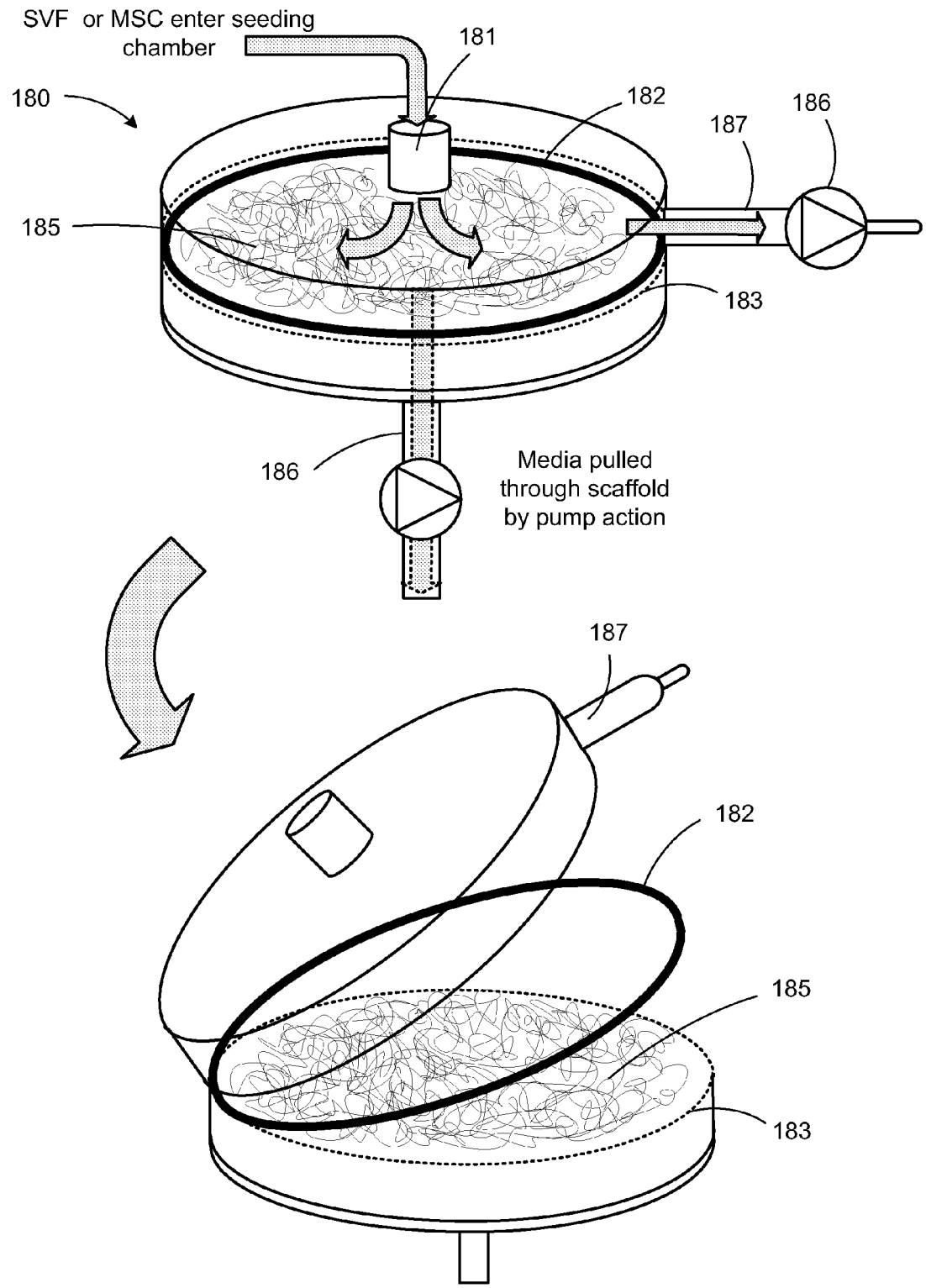
FIG. 19 depicts removal of a scaffold from a seeding chamber in accordance with one embodiment of the invention.

FIGS. 18A and B and FIG. 19 depict alternative embodiments of seeding chambers. If used in an integral fashion with the cell separator as depicted for example in FIGS. 7 and 8, the SVF fraction is removed from under the lipid containing layer in the lipid separating chamber and the SVF cells are pulled or pushed into the seeding chamber 180 by the action of a pump (not shown) that can be placed either up or downsteam of the seeding chamber. For example, where a porous scaffold is used, the cells can be forced into rapid contact with the surface of the scaffold when the fluid medium containing the cells is pulled through the scaffold. After a contact time whereby a desired % of the desired cells have adhered to the scaffold, nonadherent cells and debris are removed through nonadherent conduit 187. In other embodiments, the seeding chamber or chambers are separate apparatus from the cell isolation apparatus.

In one embodiment, the seeding chamber 180 is a disposable unit that is loaded with the scaffold 185 before the cell isolation begins. The shape and size of this scaffold is adaptable to its intended clinical use, including shape and dimension and two or three dimensional configuration.

FIG. 18A depicts one embodiment of a seeding chamber 180 wherein cells to be seeded onto scaffold 185 are introduced into seeding chamber 180 through inlet 181. In the depicted embodiment, scaffold 185 is mounted in the chamber in such a way that a fluid entering the chamber from inlet 181 may not leave through outlet 186 without passing through the scaffold 185. In the depicted embodiment, the scaffold 185 is supported by porous support 190. The chamber is designed so that no fluids can pass to outlet 186 without going through the scaffold 185. In this way, a pump or other partial vacuum source (not shown) disposed in fluid communication with outlet 186 is able to pull fluids through the scaffold and any cells entering the chamber will be rapidly pulled into contact with the scaffold. In the embodiment depicted in FIG. 18A, the top of the chamber includes a plurality of ribs 194 that are arrayed to convey fluid entering the chamber down channels 192 such that cells are relatively evenly dispersed over the scaffold surface. The top and bottom aspects of the chamber are connected by a resealable closure such as threaded closure 195, which enables ready opening of the chamber for insertion of the scaffold as well as removal of the cell seeded scaffold.

Figure 18B:
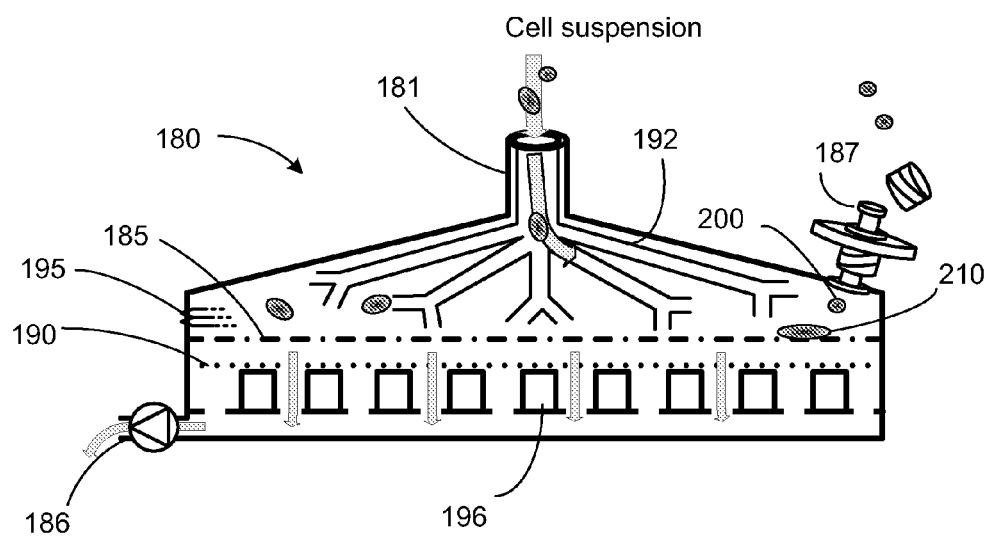

FIG. 18B depicts an alternative embodiment of a seeding chamber 180. Again cells to be seeded onto scaffold 185 are introduced into seeding chamber 180 through inlet 181. In the depicted embodiment, the upper portion of the chamber includes a port 187 whereby media can be exchanged, additive introduced, and cells that do not adhere to the scaffold can be drawn off after an incubation period. In the embodiment depicted in FIG. 18B, cells are relatively evenly distributed over the scaffold by a plurality of channels 192 that are manufactured into the lid or top of the chamber. Also in the depicted embodiment, the scaffold 185 is supported by a plurality of supports 196. Porous support 190 may not be necessary or desired. In one embodiment, the supports 196 represent the upper aspect of a grid or spiral or labyrinthine form having a plurality of drainage holes. The flow of fluid through the scaffold is essentially perpendicular to the plan of the scaffold as depicted by the arrows.

FIG. 19 depicts a seeding chamber according to one embodiment of the invention. Cells to be seeded onto porous scaffold 185 are introduced into seeding chamber 180 through inlet 181. In the depicted embodiment, porous scaffold 185 is mounted in the chamber in such a way that a fluid entering the chamber from inlet 181 may not leave through outlet 186 without passing through the scaffold 185. In one embodiment, a sealing ring 182 ensures that no fluids can pass to outlet 186 without going through the scaffold 185. In this way, a pump or other partial vacuum source (not shown) disposed in fluid communication with outlet 186 is able to pull fluids through the scaffold and any cells entering the chamber will be rapidly pulled into contact with the scaffold. Typically, as depicted in FIG. 19 the chamber 180 is constructed such that it can be opened after cells have been deposited on the scaffold and the scaffold removed for implantation or further processing.

Regardless of the embodiment used to practice the present invention, the apparatus of the present invention, as well as its associated components, may be packaged in kit form. Such a kit may, in conjunction with instructions, be operable by a trained technician for the rapid isolation of stem cell populations. In one example, the components of the apparatus can also be inexpensive and disposable.

From the foregoing description, one skilled in the art can easily ascertain the essential characteristics of this invention, and without departing from the spirit and scope thereof, can make various changes and modifications of the invention to adapt it to various usages and conditions. The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

What is claimed is:

1. An apparatus for isolating non-lipid filled cells from adipose tissue comprising:
    a chamber adapted to receive and dissociate the adipose tissue into a dissociated mixture including cells and cell clusters;
    a lipid separating unit in fluid communication with the chamber and adapted for phase separation of the dissociated mixture into a lipid layer and an aqueous non-lipid filled cellular layer without centrifugation, said lipid separating unit having at least one dispersing port equipped with a plurality of dispersing pores through which the dissociated cell mixture enters the lipid separating unit, wherein said dispersing port is disposed proximally to a bottom inner surface of the lipid separating unit; and
    at least one dispersing filter disposed in the fluid communication between the chamber and the lipid separating unit.

2. The apparatus of claim 1, wherein the chamber is divided by a mesh into a post-digestion chamber and a predigestion chamber and a recirculating fluid path through the pre-digestion and post-digestion chambers is provided via a recirculating tubing circuit.

3. The apparatus of claim 1, wherein a motive force for a fluid flow through the apparatus is provided by one or more pumps.

4. The apparatus of claim 2, wherein a heat exchanger is disposed in functional communication with the recirculating tubing circuit and fluid is directed through the heat exchanger by the motive force of the one or more pumps.

5. The apparatus of claim 4, wherein the one or more pumps and the heating exchanger are external to the apparatus and the apparatus is a one-time use disposable unit.

6. The apparatus of claim 2, wherein the mesh is fixed in a vertical cylindrical orientation.

7. The apparatus of claim 1, wherein at least one dispersing filter is disposed in a horizontal plane and is arranged in a perpendicular orientation to the mesh.

8. The apparatus of claim 2, wherein the mesh has a larger pore size than the at least one dispersing filter.

9. The apparatus of claim 1, wherein the chamber and lipid separating unit form an integrated columnar apparatus that is fully disposable.

10. The apparatus of claim 1, wherein a bottom of the chamber forms a top of the lipid separating unit.

11. The apparatus of claim 1 further comprising a cell seeding chamber in fluid communication with an outlet from the lipid separating unit.

12. A method for isolating non-lipid filled cells from adipose tissue comprising:
    introducing adipose tissue into a chamber of the apparatus of claim 1;
    dissociating the adipose tissue into a dissociated cell mixture including cells and cell Clusters;
    filtering the dissociated cell mixture through the dispersing filter disposed in the fluid communication between the chamber and the lipid separating unit;
    introducing said filtered, dissociated mixture into the lipid separating unit through the at least one dispersing port, the at least one dispersing port equipped with a plurality of dispersing pores and disposed proximally to a bottom inner surface of the lipid separating unit;
    allowing a top lipid layer form in the lipid separating unit; and
    withdrawing non-lipid filled cells from under the top lipid layer, wherein the lipid separating unit is not subject to centrifugation.

13. The method of claim 12, further comprising agitating the chamber during dissociation of the tissue.

14. The method of claim 12, wherein the adipose tissue is of human, equine, murine, porcine, canine, feline, simian, caprine, or ovine origin.

* * * * *